US008678991B2

(12) United States Patent
Rosenblatt

(10) Patent No.: US 8,678,991 B2
(45) Date of Patent: **\*Mar. 25, 2014**

(54) SYSTEM FOR TREATMENT OF ANAL INCONTINENCE

(75) Inventor: Peter L. Rosenblatt, Newton, MA (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/438,556

(22) Filed: Apr. 3, 2012

(65) Prior Publication Data

US 2012/0215060 A1  Aug. 23, 2012

Related U.S. Application Data

(63) Continuation of application No. 12/369,415, filed on Feb. 11, 2009, now Pat. No. 8,172,745, and a continuation-in-part of application No. 11/765,761, filed on Jun. 20, 2007, now Pat. No. 7,794,385, and a continuation-in-part of application No. PCT/US2005/046201, filed on Dec. 20, 2005.

(60) Provisional application No. 61/027,702, filed on Feb. 11, 2008, provisional application No. 60/868,850, filed on Dec. 6, 2006, provisional application No. 60/637,665, filed on Dec. 20, 2004, provisional application No. 60/673,878, filed on Apr. 22, 2005.

(51) Int. Cl.
*A61F 2/00* (2006.01)

(52) U.S. Cl.
USPC ............................................. 600/30

(58) Field of Classification Search
USPC ......... 600/29–32, 37; 128/897–898, DIG. 25; 606/119, 148, 222–225
See application file for complete search history.

(56) References Cited

U.S. PATENT DOCUMENTS 3,789,828 A   2/1974  Schulte et al.
6,599,235 B2  7/2003  Kovac
(Continued)

FOREIGN PATENT DOCUMENTS

| EP | 0639355 A1 | 2/1995 |
| FR | 2852817 A1 | 10/2004 |
| WO | 92/06652 A1 | 4/1992 |
| WO | 03013392 A1 | 2/2003 |
| WO | 2004/030746 A1 | 4/2004 |

OTHER PUBLICATIONS

Frederick L. Greene. MD, "Repair of Rectal Prolapse Using a Puborectal Sling Procedure," Arch. Surg., vol. 118, Apr. 1983; pp. 398-401.

(Continued)

*Primary Examiner* — John Lacyk
(74) *Attorney, Agent, or Firm* — Barbara A. Wrigley; Oppenheimer Wolff & Donnelly LLP

(57) ABSTRACT

A method of treating anal incontinence in a patient comprises providing a sling having a central portion and first and second arms, creating a subcutaneous tunnel between a first buttock incision and a second buttock incision in the patient, mechanically widening the subcutaneous tunnel to create a pocket for the central portion of the sling, grasping the first arm of the sling and pulling the sling through the subcutaneous tunnel such that the central portion of the sling rests underneath the ano-rectum, inserting an introducer needle through a first thigh incision formed in the patient and advancing the introducer needle through the first buttock incision, pulling the first sling arm through the first thigh incision, inserting the introducer needle through a second thigh incision formed in the patient and advancing the introducer needle through the second buttock incision, and pulling the second sling aim through the second thigh incision.

32 Claims, 43 Drawing Sheets

(56) References Cited

U.S. PATENT DOCUMENTS

| | | | |
|---|---|---|---|
| 7,070,556 | B2 | 7/2006 | Anderson et al. |
| 7,070,558 | B2 | 7/2006 | Gellman et al. |
| 7,351,196 | B2 | 4/2008 | Goldmann et al. |
| 7,351,197 | B2 | 4/2008 | Montpetit et al. |
| 7,407,480 | B2 | 8/2008 | Anderson et al. |
| 7,410,460 | B2 * | 8/2008 | Benderev ............ 600/30 |
| 7,722,527 | B2 | 5/2010 | Bouchier et al. |
| 7,766,926 | B2 | 8/2010 | Bosley, Jr. et al. |
| 7,794,385 | B2 * | 9/2010 | Rosenblatt ............ 600/30 |
| 8,172,745 | B2 | 5/2012 | Rosenblatt |
| 8,449,447 | B2 * | 5/2013 | Rosenblatt ............ 600/30 |
| 2004/0039453 | A1 | 2/2004 | Anderson et al. |
| 2004/0215054 | A1 | 10/2004 | Siegel et al. |
| 2009/0259092 | A1 | 10/2009 | Ogdahl et al. |
| 2011/0112357 | A1 | 5/2011 | Chapman et al. |

OTHER PUBLICATIONS

Ahmed Shafik, "Puborectoplasty: New Technique for the Repair of Fecal Incontinence," Dig, Surg. 1991:8:182-186.

International Search Report for WO 2006/069078 A3 (Date of Mailing. Aug. 13, 2007); 2 pages.

Supplementary Partial European search report for European Patent Application No. 05854848.8-1257/1827338; PCT/US2005046201 (Date of Mailing: Jul. 27, 2009): 4 pages.

Notice of Final Rejection for Japanese Patent Application No. 2007-547029, (Date of mailing: Dec. 16, 2011); 8 pages total.

Office Action issued on corresponding Canadian Patent Application Serial No. 2591493, dated Jul. 5, 2013, Canadian Patent Office, 4 pages.

Office Action issued on corresponding Canadian Patent Application Serial No. 2591493, dated Aug. 27, 2012, Canadian Patent Office, 2 pages.

* cited by examiner

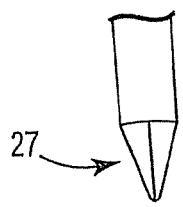 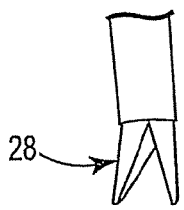 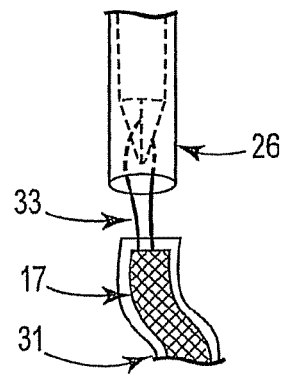
Fig. 10  Fig. 11  Fig. 12
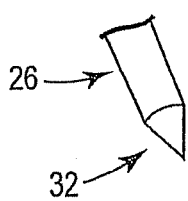 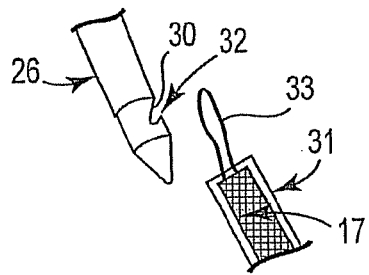 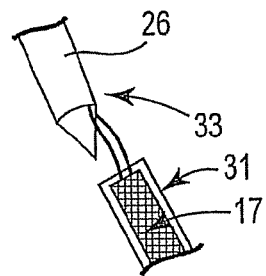
Fig. 13  Fig. 14  Fig. 15
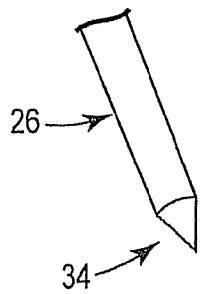 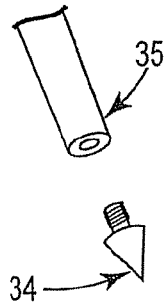 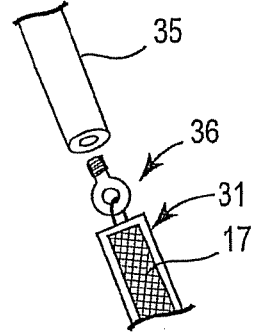
Fig. 16  Fig. 17  Fig. 18

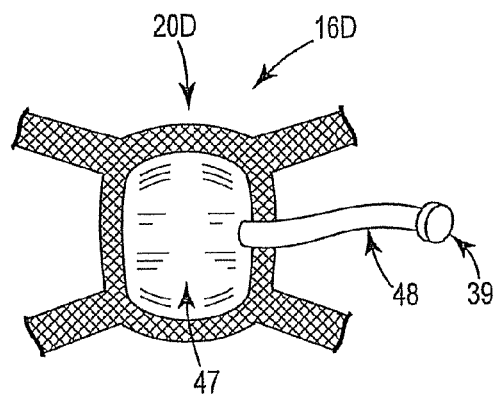
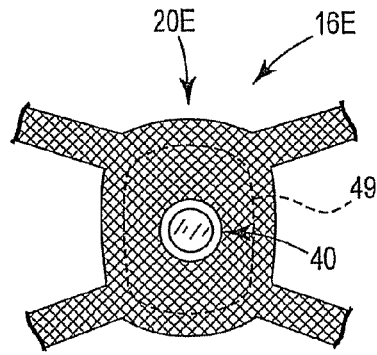
Fig. 27    Fig. 28
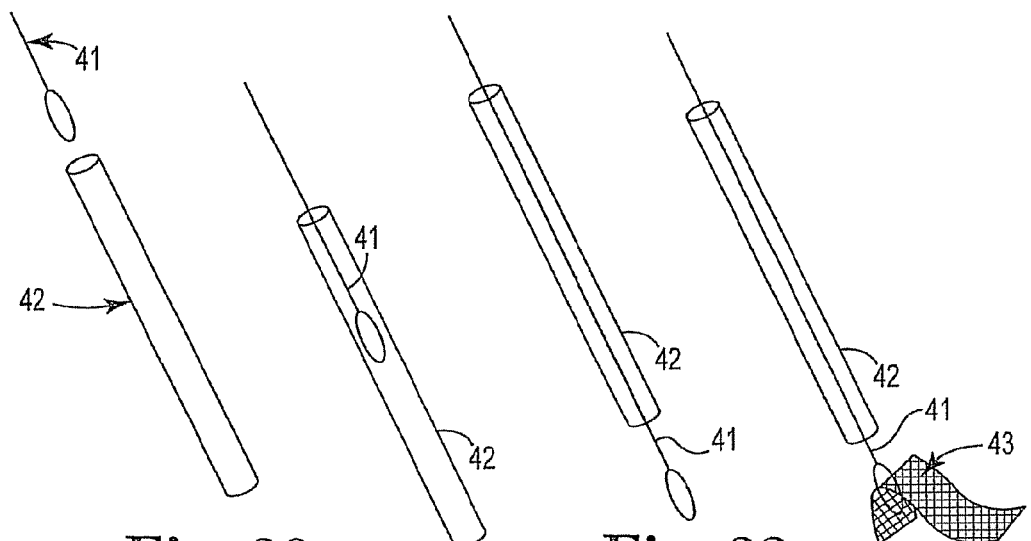
Fig. 30    Fig. 31    Fig. 32    Fig. 33

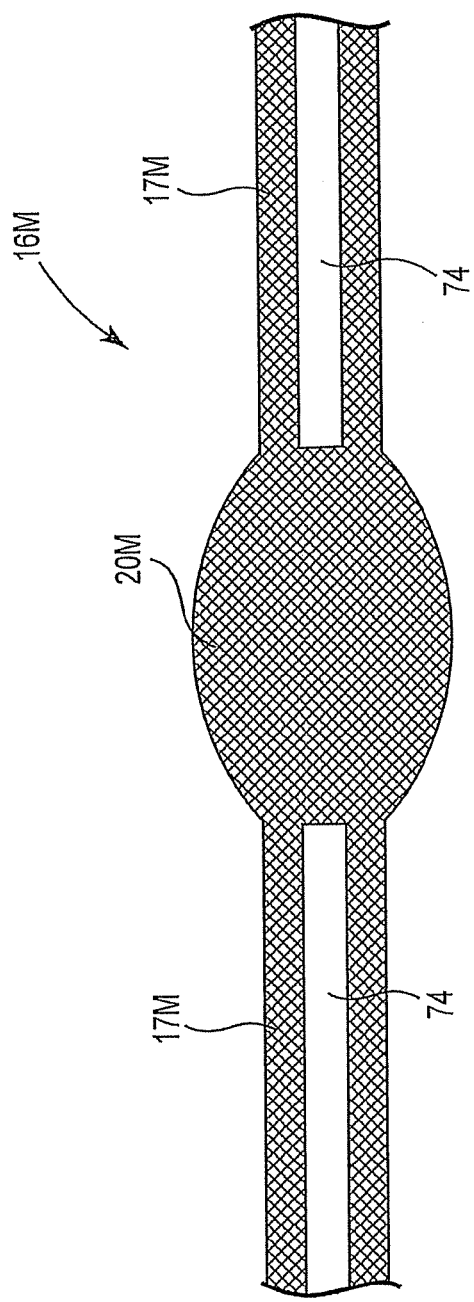

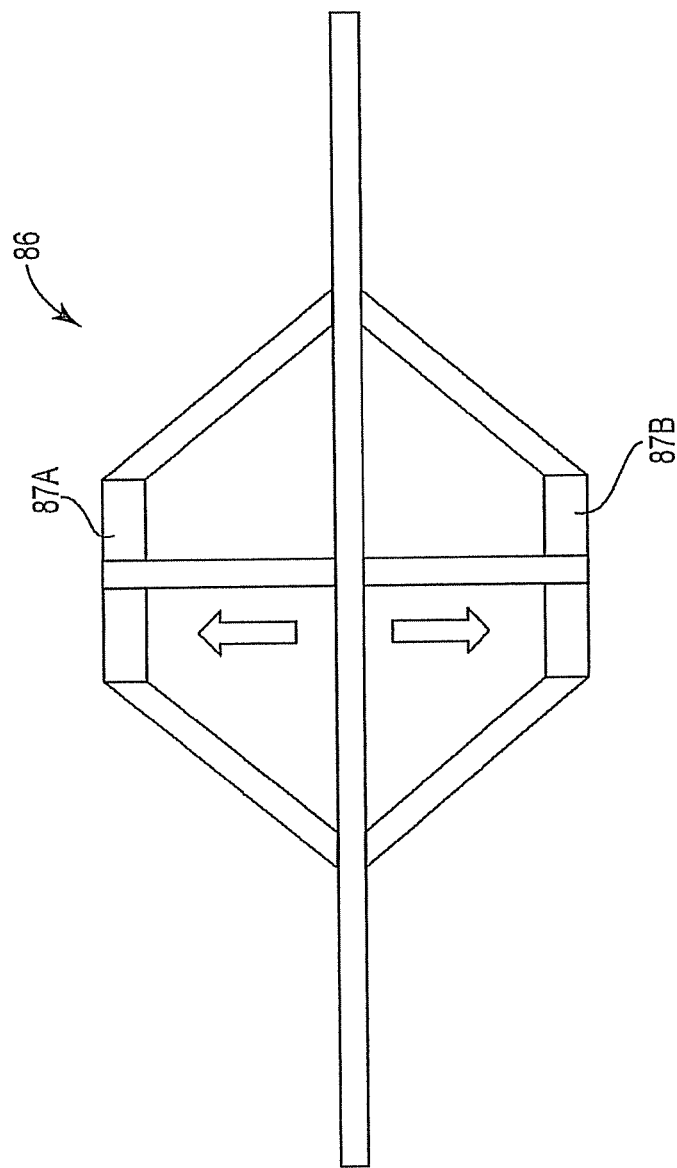

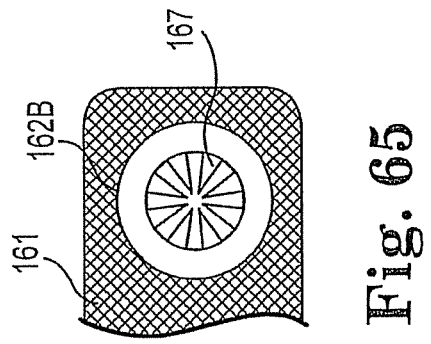
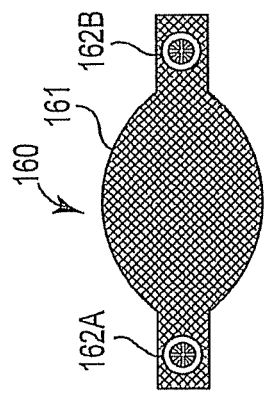
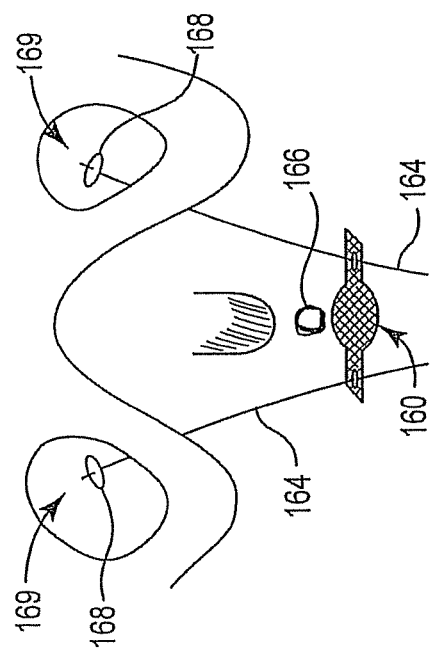

SYSTEM FOR TREATMENT OF ANAL INCONTINENCE

CROSS REFERENCE TO RELATED APPLICATIONS

This application is a continuation of U.S. application Ser. No. 12/369,415, now U.S. Pat. No. 8,172,745, issued on May 8, 2012 filed Feb. 11, 2009, which claims benefit of U.S. Provisional Application No. 61/027,702, filed on Feb. 11, 2008, and which is a continuation-in-part of U.S. application Ser. No. 11/765,761, filed Jun. 20, 2007, now U.S. Pat. No. 7,794,385, issued on Sep. 14, 2010, which claims benefit of U.S. Provisional Application No. 60/868,850, filed Dec. 6, 2006, and which is a continuation-in-part of PCT Application No. PCT/US2005/046201, filed Dec. 20, 2005, which claims the benefit of U.S. Provisional Application No. 60/637,665, filed Dec. 20, 2004, and which claims the benefit of U.S. Provisional Application No. 60/673,878, filed Apr. 22, 2005; the entireties of which are hereby incorporated by reference.

BACKGROUND OF THE INVENTION

Anal incontinence is a common problem that occurs in both men and women, though is certainly more prevalent in women after vaginal childbirth, presumably the result of trauma to pelvic floor muscles, supporting fascia and nerves. Fecal incontinence affects an estimated 7.6 percent of women between the ages of 30-90. The prevalence increases with age, affecting 3.6 percent of women between 30-39 and 15.2 percent of women between 80-90. Several factors contribute to anal continence, including the resting tone of the external and internal anal sphincters, as well as the position of the levator ani muscles, especially the puborectalis muscle, which forms a sling around the rectum and is responsible for the so-called "ano-rectal angle," which keeps stool in the rectum until voluntary defecation relaxes the puborectalis muscle and straightens the angle, allowing stool to move towards the anus.

Defecation is often aided by expulsive abdominal forces. Anal incontinence may occur as the result of several mechanisms, including direct damage to the internal or external anal sphincters (from iatrogenic episiotomy or spontaneous lacerations during vaginal delivery), or to the levator ani muscles. It may also result from indirect injury of these muscles through denervation of the nerves that supply these muscles. Treatment of this problem has centered on pelvic floor rehabilitation, dietary changes, or surgical correction. Surgery has been used to treat specific defects in the anal sphincters, such as external anal sphincteroplasty. Success rates of only 50% or less are generally reported for these procedures on long-term follow-up.

More recently, an artificial anal sphincter has been used to bypass these muscles, though this surgery involves fairly extensive dissection and requires the patient to depress a subcutaneous valve which temporarily deflates the sphincter cuff and allows voluntary defecation. This procedure is performed in very few centers in the U.S., and even in experienced hands, complications occur frequently. Dynamic graciloplasty, which involves mobilization and wrapping of the gracilis muscle around the ano-rectum is now another accepted procedure although it remains complex and requires extensive experience to obtain good results. More recently, sacral nerve stimulation has been used with some success to treat fecal incontinence, though the mechanism of success in these patients remains unclear, and may not be appropriate in women with obvious anatomic abnormalities, such as anal sphincter or levator muscle disruptions.

In addition, many women report other symptoms of bowel dysfunction, such as constipation and incomplete bowel emptying. For some women, these symptoms are due to either an anterior rectocele (a hernia of the rectum into the vaginal canal), or due to a defect in the levator ani muscles, which results in descent of the levator plate and/or perineum with abdominal straining. In addition, patients may be noted to have a defect in the posterior aspect of the rectum, or a posterior rectocele. There are very few treatment options for this condition, though retrorectal levatorplasty has been used in the past. In this procedure, an incision is made between the anus and the coccyx and the levator muscles are exposed bilaterally. Sutures are then placed in the levator muscles to plicate them together in the midline.

Pelvic organ prolapse is a condition where organs, such as the uterus, the rectum, or the bladder, fall down or slip out of place within a person's body. It is commonly used in reference to organs protruding through a woman's vagina, but prolapse may occur within men as well. In general, the levator ani muscles provide the main support for pelvic organs including, for example, the rectum, the vagina, and the urethra. In a person with a normal pelvis, the levator ani muscles keep the pelvic floor closed, thereby allowing the pelvic and abdominal organs to rest on the levator ani muscles. This also significantly reduces the tension that would otherwise be placed on the fascia and ligaments that support the pelvic organs. The posterior portion of the levator ani muscles arise from the area of the tendinous arch. The anterior portion of the levator ani muscles arise from the superior pubic rami and from the anterior end of the obturator internus muscles. This portion forms the pubococcygeus muscle and the puborectalis muscle. The pubococcygeus muscle is a generally thick, U-shaped muscle through which the urethra, vagina, and rectum transverse. The pubococcygeus muscle supports these structures at rest, and helps to augment the endopelvic fascia during coughing or straining. The puborectalis muscle is structured to act as a sling support for the rectum, and includes two ends that attach to the anterior side of the symphysis pubis. The levator ani muscle group includes an opening through which the vagina and urethra pass, which is referred to as the urogenital hiatus. Similarly, the levator ani muscle group includes an opening through which the rectum passes, which is referred to as the rectal hiatus.

In a normal woman, the pelvic floor muscles support most of the weight of the pelvic organs, such as the vagina, uterus, bladder, and rectum. Additionally, the various pelvic fascia and ligaments stabilize these structures in position. When the natural anatomic relationships in the pelvis are disrupted, or if injuries occur, dysfunctions such as urinary incontinence, fecal incontinence, or prolapse of the pelvic organs, may occur. For example, if one of the levator ani muscles is damaged, the muscle may be unable to adequately support the weight of the pelvic organs. This will result in a disproportionate amount of the pelvic organ weight being placed onto the pelvic ligaments, which are significantly weaker than the fibrous tissue of the ligaments that connect bones. In particular, the pelvic ligaments are more accurately described as thickening of the endopelvic fascia tissue, which is composed of collagen, smooth muscle, elastin, and fibrovascular bundles. These ligaments are not designed to carry the increased load resulting from problems in the pelvic floor. As a result, these ligaments may eventually fail. The failure or damage to the pelvic floor ligaments may cause, for example, the bladder, rectum, or uterus to prolapse through the vagina.

Similarly, expansion of or damage to the levator or rectal hiatus may result in the bladder, vagina, or rectum prolapsing through the hiatus.

As stated previously, pelvic prolapse conditions result from the weakness or damage to the normal pelvic-support systems. In general, the main categories of pelvic prolapse include cystocele, rectocele, enterocele, uterine prolapse, and vaginal vault prolapse. The most common causes of these pelvic floor disorders in a female patient include child birth and removal of the uterus (hysterectomy). However, other contributing factors may include connective tissue defects, prolonged heavy physical labor, postmenopausal atrophy, neurogenic weakness of muscles, muscle weakness due to aging, and obesity.

A cystocele occurs when damage to the pubocervical fascia in the central or lateral areas (or both) allows the bladder to protrude into the vagina. Simply defined, a cystocele is a protrusion of the bladder into the vagina due to defects in pelvic support.

A rectocele is a bulge into the vagina caused by the rectum prolapsing through an attenuated rectovaginal septum. A rectocele is commonly a result of childbirth or chronic constipation. During childbirth, the rectovaginal septum and surrounding vaginal tissues are stretched and disrupted, which may cause weakness and stretching in these tissues. A rectocele typically forms a pocket just above the anal sphincter where stool may become trapped.

An enterocele is essentially a herniation of the small bowel into the vagina. Specifically, the peritoneal sac containing a portion of the small bowel extends into the rectovaginal space between the posterior surface of the vagina and the anterior surface of the rectum.

A uterine prolapse is the distention of the uterus and cervix outside the vagina. It is often associated with a rectocele, cystocele, or entrocele.

Finally, a vaginal vault prolapse is the distention of the vaginal apex after hysterectomy outside the vagina. It is also often associated with a rectocele, cystocele, or entrocele.

What is needed is an improved system and method for the treatment of anal incontinence and defecatory dysfunction, as well as pelvic organ prolapse.

BRIEF SUMMARY OF THE INVENTION

The present disclosure describes systems and methods for treating anal incontinence and other types of defecatory dysfunction, such as perineal descent, constipation, incomplete bowel emptying, and rectal prolapse. The present disclosure also describes systems and methods for treating pelvic organ prolapse and other pelvic floor disorders. Some disclosed systems and methods particularly facilitate minimally-invasive treatment of anal incontinence, defecatory dysfunction, and pelvic organ prolapse.

In accordance with one aspect of the present invention, a method of treating anal incontinence in a patient is disclosed that comprises the steps of providing a sling having a central portion and first and second arms, creating a subcutaneous tunnel between a first buttock incision and a second buttock incision in the patient, mechanically widening the subcutaneous tunnel to create a pocket for the central portion of the sling, grasping the first arm of the sling and pulling the sling through the subcutaneous tunnel such that the central portion of the sling rests underneath the ano-rectum, inserting an introducer needle through a first thigh incision formed in the patient and advancing the introducer needle through the first buttock incision, pulling the first sling arm through the first thigh incision, inserting the introducer needle through a second thigh incision formed in the patient and advancing the introducer needle through the second buttock incision, and pulling the second sling arm through the second thigh incision.

In accordance with another aspect of the present invention, a sling is disclosed that comprises a central portion having a first end and a second end, a first connector coupled to the first end of the central portion, a first sling arm structured to be received by the first connector, a second connector coupled to the second end of the central portion, and a second sling arm structured to be received by the second connector. The first and second connectors may include, for example, ring-shaped members having a plurality of tines that are structured to engage with the sling arms.

In accordance with yet another aspect of the present invention, a sling is disclosed that comprises a central portion having a first end, a second end, a superior surface, and an inferior surface, a first sling arm extending from the first end of the central portion, a second sling aim extending from the second end of the central portion, and an adjustable device coupled to the inferior surface of the central portion, the adjustable device including a housing and adjustment means coupled thereto, wherein the adjustable device is structured to adjust a tension of the first and second sling arms.

BRIEF DESCRIPTION OF THE DRAWINGS

FIGS. 10-18 depict exemplary uses of various instruments to position a sling or length of supporting material.

FIGS. 24-29 depict exemplary sling embodiments having fluid-filled sacs.

FIGS. 30-33 depict an exemplary use of a stylet having a loop.

FIGS. 44A-44B demonstrate alternative sling embodiments illustrating the use of "less elastic" sections of material in one or more areas of the sling.

FIG. 49 demonstrates a mechanical device that can be used to tunnel between two buttock incisions and then spring open to dilate the path.

FIGS. 63-64 illustrate an alternative embodiment of a sling in accordance with another aspect of the present invention, wherein a central portion of the sling includes a pair of rings structured to receive a corresponding pair of sling aims.

FIG. 65 is an enlarged view of one of the pair of rings illustrated in FIGS. 63-64.

DETAILED DESCRIPTION OF THE INVENTION

Figure 1:
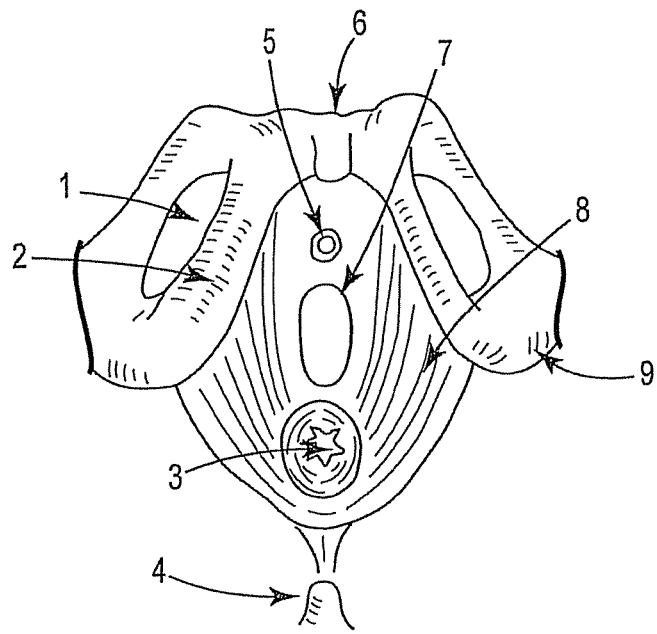
FIG. 1 depicts the anatomy of the bony pelvis.

The present disclosure provides a variety of systems and methods for treating anal incontinence, defecatory dysfunction and pelvic organ prolapse. The normal ano-rectal angle can be restored by inserting a disclosed device under the posterior rectum, which may be supported with a synthetic or natural material in a sling-like position behind the anus and/or rectum. A posterior supporting apparatus may provide partial or complete closure of the rectum and/or anus with the posterior supporting apparatus.

In one embodiment, a synthetic or natural sling material may be placed under the rectum and may be supported by its aims, which may be extended up in a sling-like fashion through the obturator foramen bilaterally, or retropubically to the suprapubic region. In another embodiment, the device placed posterior to the rectum may include one or more inflatable or fluid-filled sacs, which may or may not be adjusted post-operatively, by either changing the position or by altering the amount of fluid material, for example saline or a hydrogel, within the sacs. "Fluid" should be understood to include gasses, liquids, and semisolid media (such as gels). In some embodiments, the central portion of the sling may have a curved shape, such as a saddle shape, to help it conform to the external contour of the anus, rectum, ano-rectal angle, and/or levator ani muscles.

In one embodiment of a method of treating anal incontinence or defecatory dysfunction, an incision may be made between the anus and the coccyx and dissection performed, whereby the levator muscles and the levator plate are exposed. A small nick may be made on the medial thigh just lateral to the ischiopubic ramus and an introducer needle may be placed through the medial thigh incision, around the ischiopubic ramus, and be directed posteriorly into the ischiorectal fossa. The needle may then be directed lateral to the levator muscles, optionally with the assistance of a surgeon palpating the instrument though the vagina. The needle may then be brought posterior to the rectum, exiting the incision that was made in the midline. Alternatively, the needle may be passed from the midline incision between the anus and coccyx to the medial thigh incision lateral to the ischiopubic ramis. In one embodiment, a suture may be threaded onto the eye of the needle, which in this case may be placed from the medial thigh to the incision between the anus and the coccyx, and may then be withdrawn through the tissue and held on the medial thigh. The procedure is repeated on the contralateral side. A synthetic (i.e., polypropylene, polyester, etc.) mesh (such as tension-free vaginal tape, TVT) or natural graft material may then be attached to each of the sutures coming from the midline incision, and the mesh may then be brought up through the medial thigh incisions by pulling up on the sutures.

The mesh may have a covering plastic sheath, which can facilitate passage through the tissues. The sheath may be removed when the sling is properly adjusted.

In another embodiment, the needle that is passed through the tissue may have a hollow sleeve or tube over it (e.g., made of plastic, metal, or the like), and after passage, the needle may be withdrawn through the tissue, leaving the hollow sleeve in place. A stylet (e.g., made of plastic, metal, or the like) may then be then placed in the tube. The stylet may have a connector, such as a hook or a loop, so that a length of supporting material, such as a synthetic mesh (e.g., made of polypropylene or the like) or a natural graft, may be attached to the stylet connector. Once this procedure is performed bilaterally, the supporting material may be positioned under the rectum and the tension on the arms of the sling may be adjusted. If the sleeves or tubes are utilized, the mesh can be adjusted before withdrawing the sleeves or tubes.

In another embodiment, two passes of the needles can be made on each side, one approximately at the level of the medial superior portion of the obturator foramen, and the other several centimeters inferior and slightly more lateral (at the inferior portion of the obturator foramen). This permits two lengths of supporting material (also called "mesh" but not necessarily limited to mesh) to be brought up on each side. These mesh strips are attached to a central mesh that may be placed under the rectum, which may be a pre-formed mesh, or may be constructed by attaching the central mesh to the four mesh strips—two on each side. The subrectal portion may be synthetic mesh, or may be made of another material, such as an inflatable or fluid-filled polymer sac. The sub-rectal element provides support to the posterior anus and/or rectum, and creates an angle between the anus and rectum, which keeps stool in the rectum until voluntary defecation.

In another embodiment, after the needle passes through the tissue, and is withdrawn, leaving a hollow tube in place, a plastic or metal stylet, previously fixed to the mesh with or without a sheath, can be placed up from the sub-rectal incision to the medial thigh incision and can be held. The mesh may then be brought up through the tubing by pulling on the stylet from above. Once the sling end comes out from the tubing, the hollow tube can be removed, after the sling has been adjusted for proper tensioning.

In another embodiment, the posterior aspect of the sub-rectal portion may be attached to the coccyx by one of several methods, such as direct suturing or with bone anchors. Such attachment can help maintain the position of the sub-rectal portion, which, in effect, restores the structure and function of the levator plate. Alternatively, the sub-rectal portion may have an extension coming off its inferior portion, which extends out and is fixed to the coccyx.

The fluid-filled sac under or adjacent to the rectum may have a port, such as a subcutaneous port, that may allow for fluid addition or removal in the post-operative period. This port may facilitate post-operative adjustment of the size and/or shape of the sac to provide for optimal results. The subcutaneous port may be placed directly under the sac, in the perineal skin, or may be connected to the sac by means of a connector tubing so that the port does not need to be located in the perineum itself, but instead may be positioned in a number of areas, including, for example, the buttocks.

The needle may have a hook near the end, that can be covered during insertion, but that may be exposed after the needle has been placed through the tissue. The user implanting the device may operate a switch or other actuator, such as a spring-loaded mechanism, to expose the hook. The arm of the sling, or a pre-loaded suture on the sling-arm, may then be placed on the hook and the needle withdrawn through the tissue.

In another embodiment, once the needle is placed through the tissue, the tip of the needle may be unscrewed off the end of the needle shaft. The of the sling may have a device attached to each end that may screw onto the needle shaft or otherwise fasten onto the needle shaft. The needle may then be withdrawn, bringing the sling arm through the tissue.

A sheath covering the needle may remain in place in order to facilitate the movement of the synthetic material through the tissue, which may be removed once the tension on the sling is adjusted. The sheath may be deformable, rather than rigid or semi-rigid, and may be flattened after removal of the needle, to accommodate the flat shape of the sling material itself.

The needle could have a blunt metallic insert (to maintain the strength of the needle) with a plastic covering sheath that has a sharp needle tip configuration on the end. After the needle is placed through the tissue, the metallic blunt needle may be withdrawn, and the plastic needle tip cut off. A suture retriever may then be placed anterograde through the hollow plastic tube in order to grasp a suture that has been attached or pre-attached to the sling. The sling may be withdrawn through the plastic tube and the tube may be removed once the sling is adjusted.

In another embodiment, the needle tip may be made from two separate pieces that act as jaws that open to catch the mesh or suture attached to the mesh, after the needle is passed through the tissue from the medial thigh to the incision posterior to the anus. This needle may be introduced with a plastic outer covering, so that the sling material may be drawn up through the tissue without catching on the surrounding structures. Once in proper position, the surgeon may remove the plastic sheath, which would then allow for the synthetic mesh to become fixed in the tissues.

A curved metal needle may be placed through the tissue from the medial thigh to the perineal incision. The end of the needle may be unscrewed, and the sling with attached plastic or metal piece may be screwed or snapped onto or into the connector on the needle. The sling, possibly with covering sheath, may then be withdrawn through the tissue and held and the plastic sheath may be removed after the sling has been adjusted.

The shape of the sling may be a fixed width throughout its length. Alternatively, the central portion that is positioned under/behind the rectum may be wider than the amts. The central portion may be curved to help it conform to the shape of the tissue it is supporting. The curved shape may be a saddle shape, such as roughly a hyperbolic paraboloid or resembling a PRINGLES® brand potato crisp. The central portion may be preformed with the curved shape.

The mesh may be continuous throughout the length of the sling, or may have a central portion that includes a fluid-filled sac that is affixed to the sling aims on the sides. Preferably, the synthetic mesh would be continuous throughout its length in order to provide a backboard of support under the rectum and under the fluid-filled sac, if the fluid-filled sac is employed.

The fluid sac may have a circular or elongated shape under the rectum, or may include several compartments that can be separately filled with several access ports, in order to change the occlusion of the rectum. The fluid filled sac may have the curved shapes as discussed above.

Wings may connect a sling central portion to the aims of the sling. The wings may be made of mesh or other supporting material.

In another embodiment, the sling may be a hybrid of materials, comprised of, for instance, a polypropylene mesh along the aims of the sling in order to have self-attaching properties to the obturator fascia, and a natural xenograft material, such as porcine small intestinal submucosa, or an allograft, such as cadaveric fascia, located under and or lateral to the anus/rectum.

In another embodiment, the arms of the sling may include a synthetic material such as silastic, polypropylene or other plastic, and may have serrations or tines that increase the ability of the aims to grab on to the obturator fascia as the aims are pulled through the tissue.

In another embodiment, the arms of the sling include sutures. There may be several sets of sutures on each side, in order to prevent the sub-rectal portion of the sling from rolling up underneath the ano-rectum.

In another embodiment, the anus of the sling may be attached to pelvic bone, such as the inferior-medial portion of the ischiopubic rami, or the inferior portion of the pubis, with bone anchors, suture material, or other fixation devices.

In another embodiment, the material under and/or lateral to the ano-rectum includes a synthetic material, such as silastic or other plastic material, that may be flexible, to conform to the shape of the bowel.

In another embodiment, a number of synthetic or natural elements are attached to the mesh in a direction transverse to the length of the sling, such as perpendicular or substantially perpendicular to the length of the sling. The elements may be semi-rigid and may be so positioned in the mesh as to be located under or lateral to the bowel when the mesh is deployed, for the purpose of keeping the mesh from rolling up underneath the ano-rectum. For example, the graft may have a stiff or flexible bar incorporated into the graft, located on either side of the rectum, to prevent rolling of the graft material. Alternatively, one or more rigid or semi-rigid elements may be attached to the sling in a direction generally parallel to the length of the sling.

In another embodiment, the sling may have additional straps attached to the subrectal portion that penetrate posteriorly, such as on either side of the coccyx, that may pass through the subcutaneous tissue and hold the graft in position, to prevent rolling of the subrectal mesh.

In another embodiment, the synthetic material may be elastic, which may permit stretching of the sling with abdominal straining, such as occurs with voluntary defecation.

In another technique, the sling may be passed through the levator ani muscle, rather than behind the muscles.

In another embodiment, the system may include a device used to evaluate the anorectal angle, for pre-operative diagnosis, intra-operative adjustment, and/or post-operative evaluation. The device is sufficiently flexible that it can be flexed to conform to the anorectal angle. The amount of flexion may be measured, thereby establishing the shape of the ano-rectal angle. In one embodiment, the device may be inserted into the rectum, and a flexible joint of the device may be placed at the junction between the anus and rectum. The device may then measure the angle created between the rectal and anal portions, and this angle may be displayed visually on the device, in one of a number of manners, including a dial or a digital display. The angle may also be communicated to an external display for convenience. The device may include a rotation or position sensitive transducer. This ano-rectal angle measurement device may be adapted so that it fits over or on the examiner's gloved finger with a portion that fits over or on the examiner's distal finger, and another portion that fits over or on the proximal finger. In this manner, when the examiner bends his or her finger to determine the ano-rectal angle, the measured angle is recorded visually on a display.

Various portions of the sling device may be coated, impregnated, or formed with one or more drugs to be eluted to an adjacent tissue. For instance, there is evidence in the literature that androgen treatment may increase the mass of the levator ani muscles. A drug eluding or impregnated sling material (such as a mesh) may be used since the sling is abutting the levator ani muscles and may improve the mass and possible function of the muscles.

Additionally, various portions of the device may be formed of biodegradable or bioabsorbable material.

According to another aspect of the present invention, an alternative method for treating anal incontinence, defecatory dysfunction, or pelvic organ prolapse includes creating a subcutaneous tunnel between two buttock incisions that are placed approximately halfway between the level of the anus and the coccyx, such as about 1.5 cm lateral to the anus. The tunnel may be widened mechanically to create a pocket, in which the sling belly or central portion may sit. The sling may be pulled through from one buttock incision to the other, and positioned so that the central portion of the sling rests under the ano-rectum. A curved introducer needle may then be placed through a small incision in the patient's inner thigh, at the level of the external urethral meatus and just lateral to the descending ischiopubic ramus (which corresponds to the medial portion of the obturator membrane). The needle may be advanced into the ischiorectal fossa, lateral to the levator ani muscles and brought through the lateral buttock incision. A connector attached to the sling ami may then be irreversibly attached to the introducer needle and the sling arm may be transferred through the thigh incision. The same procedure may be performed on the contralateral side. Tension may be adjusted on the sling, and the plastic sleeves may be removed, leaving the sling in place supporting the posterior ano-rectum. Finally, the sling arms may be cut at the level of the skin and the four incisions may be closed in standard fashion with either sutures or glue.

Turning now to the figures, FIG. 1 is a diagram illustrating the anatomy of the bony pelvis, including the pubic symphysis 6, the ischiopubic ramus 2, the ischial tuberosity 9, the coccyx 4, and the obturator foramen 1. FIG. 1 also demonstrates the relationship of the levator ani muscles (and, in particular, the puborectalis 8) to the urethra 5, vagina 7, and rectum 3.

Figure 2:
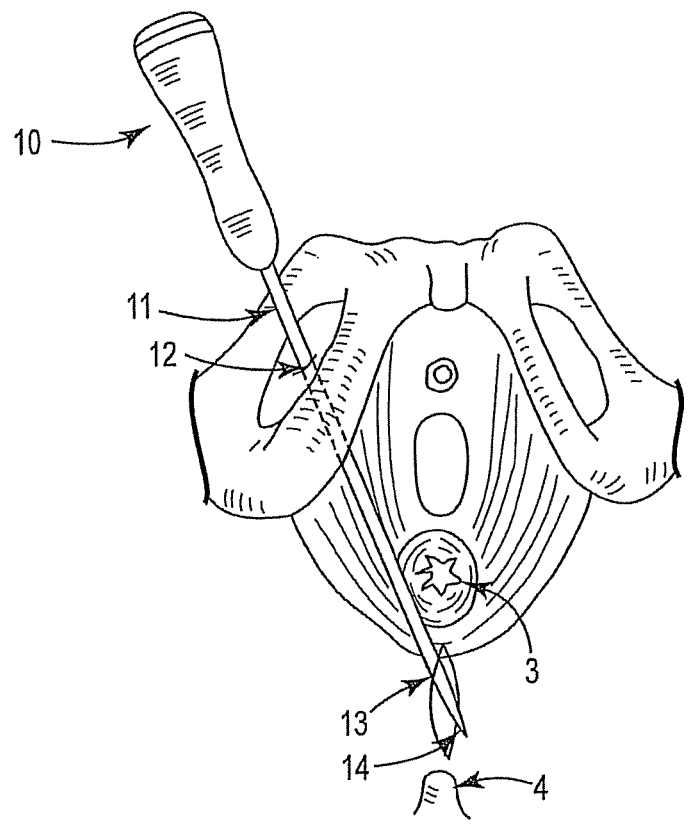
FIG. 2 depicts an exemplary placement of a needle device in the pelvis.

FIG. 2 is a diagram outlining a first surgical procedure using a needle 11 with a handle 10 attached thereto in order to tunnel between a medial thigh incision 12, through the obturator membrane, and into the ischiorectal fossa. As illustrated in FIG. 2, a needle tip 14 eventually emerges through a vertical incision 13 between the rectum 3 and the coccyx 4.

Figure 3:
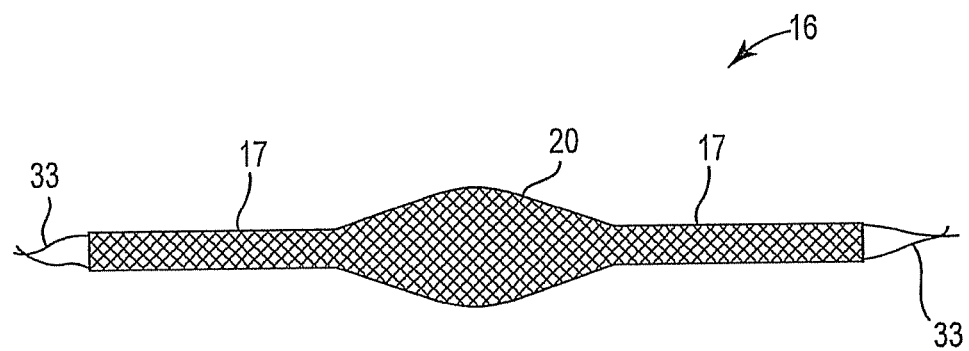
FIG. 3 illustrates one exemplary embodiment of a sling in accordance with the present invention

FIG. 3 illustrates one exemplary embodiment of a sling 16 in accordance with the present invention. Sling 16 generally includes a pair of aims 17 and a belly or central portion 20 disposed between the pair of arms 17. Particularly, the wider central portion 20 disposed between the narrower arms 17 may be structured such that it may sit under the rectum 3 and distribute forces over a wide area. As illustrated in FIG. 3, both the arms 17 and the central portion 20 of the sling 16 are formed from a mesh material, although numerous other configurations are contemplated as disclosed herein and as will be appreciated by those skilled in the art. Additionally, the central portion 20 of the sling 16 does not have to be structured with a width that is greater than a width of the arms 17.

As illustrated in FIG. 3, each of the arms 17 may have a suture loop 33 extending therefrom. Although not necessary, suture loops 33 may assist the surgeon in placement of the aims 17 by providing an element that may be grasped by the needle 11.

Figure 4:
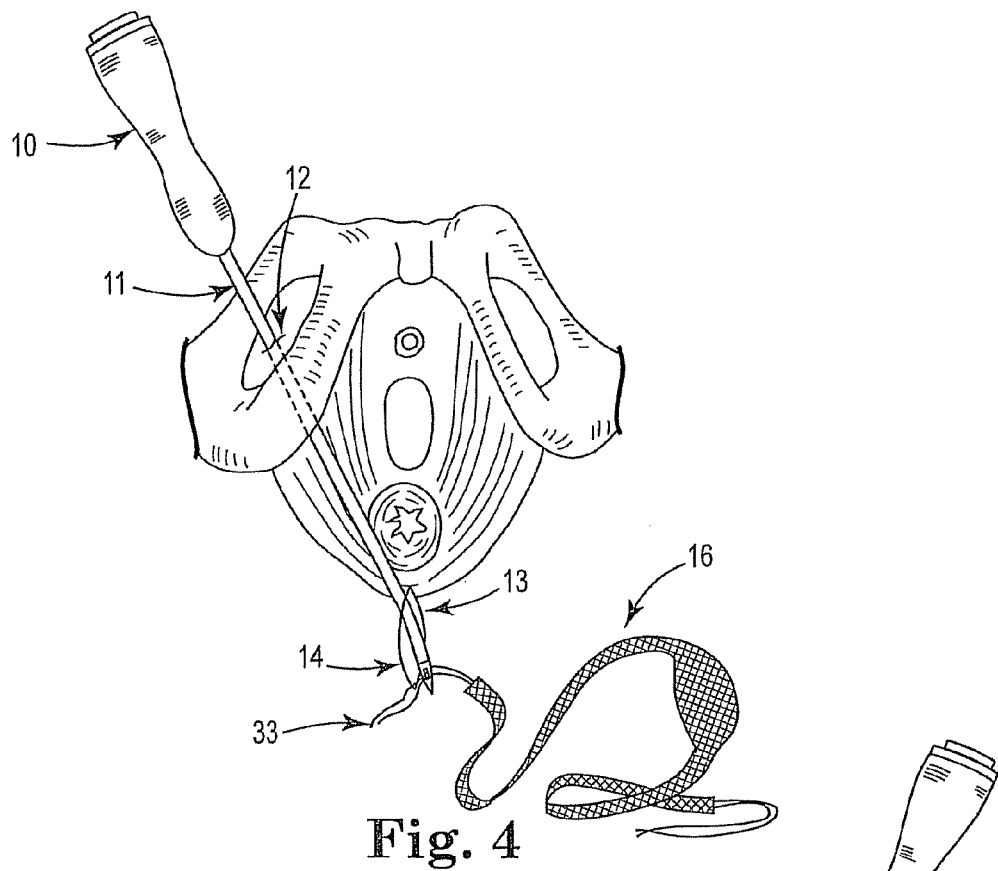
FIGS. 4-5 depict steps in one exemplary placement method of the sling of FIG. 3.
Figure 5:
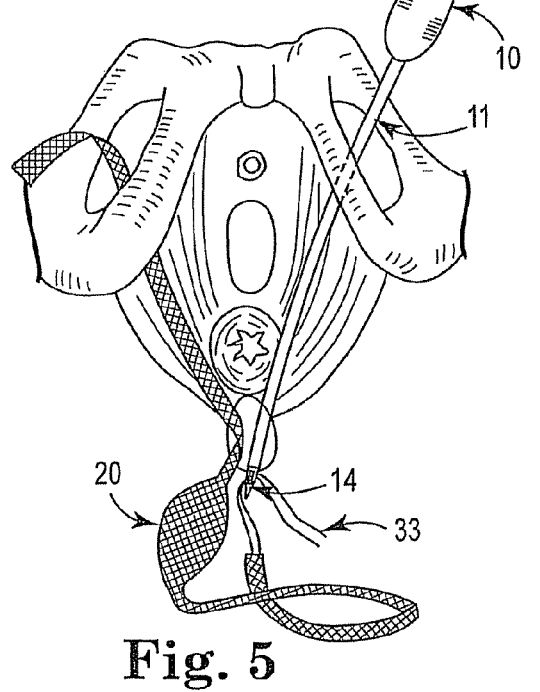

FIGS. 4-5 depict steps in one exemplary placement method in accordance with the present invention. As illustrated in FIG. 4, the needle 11 with the attached handle 10 has been placed through a first medial thigh incision 12, the obturator foramen, the ischio-rectal fossa, and out through the incision 13 between the rectum and the coccyx. A suture loop 33 attached to the sling arm 17 may be grasped by the needle tip 14 in order to transfer the sling to the thigh incision 12. FIG. 5 illustrates the second pass of the needle on the contralateral side with the handle 10 and needle 11 in place. The tip 14 may grasp the suture loop 33 on the second aim 17 in order to pull the other arm of the sling up through to the thigh incision. This allows the central portion 20 of the sling 16 to rest under the ano-rectal area.

Figure 6:
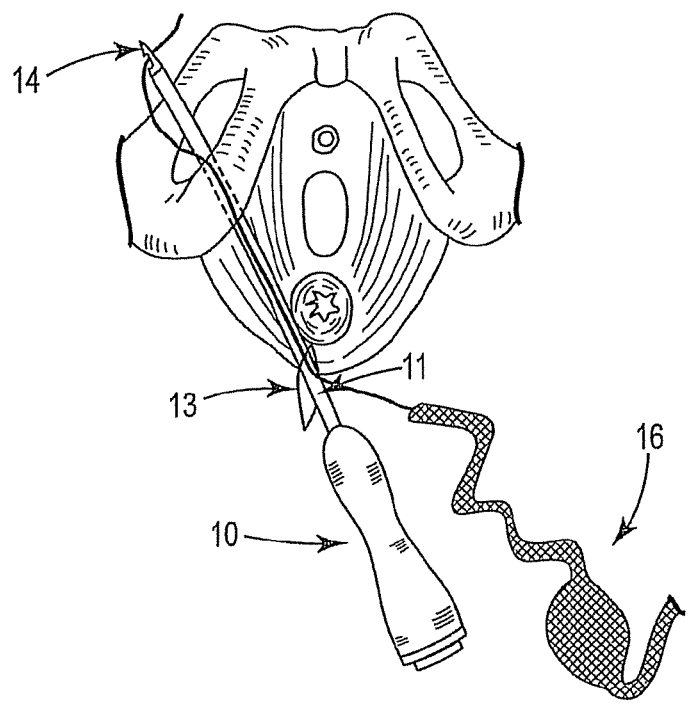
FIGS. 6-7 depict steps in another exemplary placement method of the sling of FIG. 3.
Figure 7:
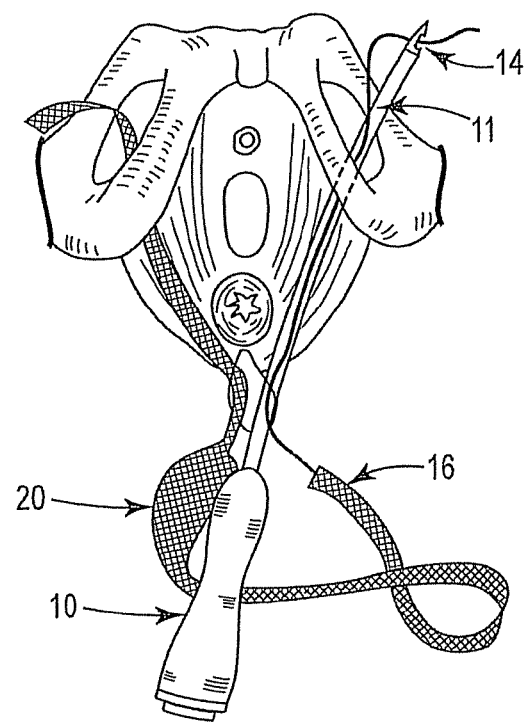

FIGS. 6-7 depict steps in another exemplary placement method. As illustrated in FIG. 6, the needle 11 with the attached handle 10 has been placed from the post-anal vertical incision 13 up through the ischiorectal fossa, through the obturator foramen, and out through the thigh incision, and has transferred a suture attached to the sling 16 to the thigh region. This allows the sling to be brought through the tissues up to the region of the thigh. FIG. 7 illustrates the right side of the sling 16 in place and the needle 11 with attached handle 10 transferring a suture attached to the left side of the sling arm 17 of the sling 16 up through the left side. The suture is being held by the needle tip 14.

Figure 8:
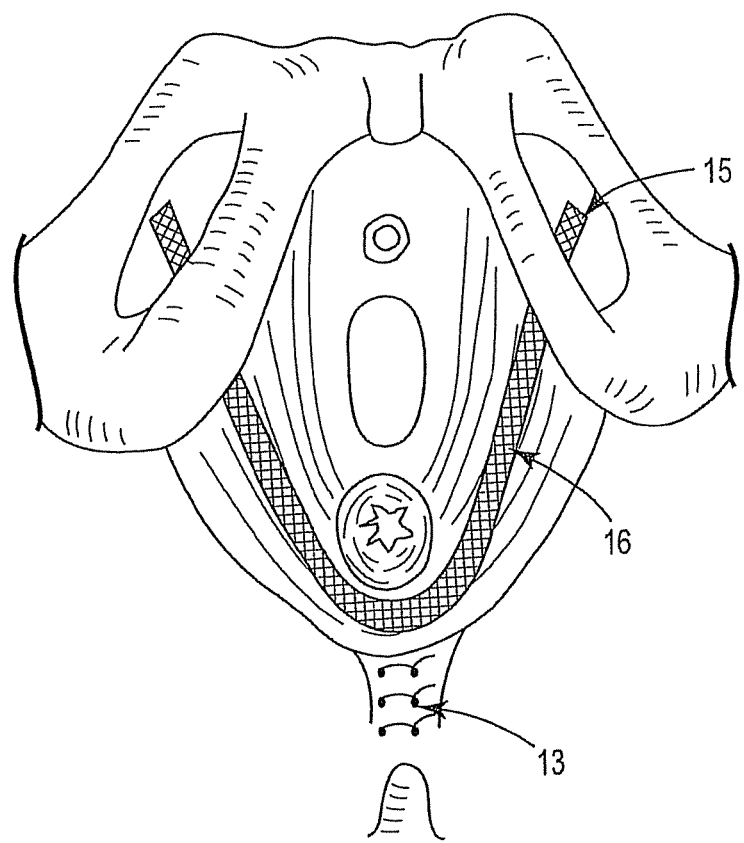
FIG. 8 depicts an exemplary final position of the sling of FIG. 3 within a patient.

FIG. 8 is a diagram illustrating a final position of the sling 16 under the anus and/or rectum. As shown in FIG. 8, the central portion of the sling is disposed between the anus and the coccyx, and the sling arms extend up through the medial portion of the obturator membrane 15.

Figure 9A:
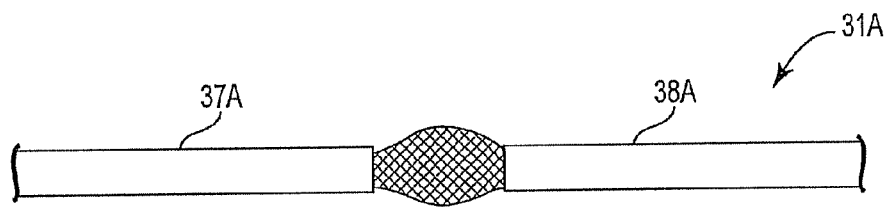
FIGS. 9A-9D illustrate various embodiments of removable sheath members structured to cover at least a portion of a sling in order to promote passage of the sling through tissue during surgical placement.
Figure 9B:
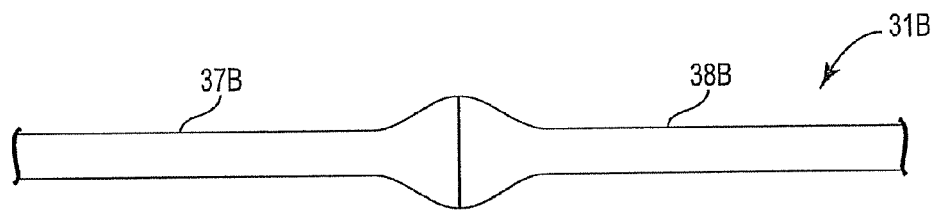
Figure 9C:
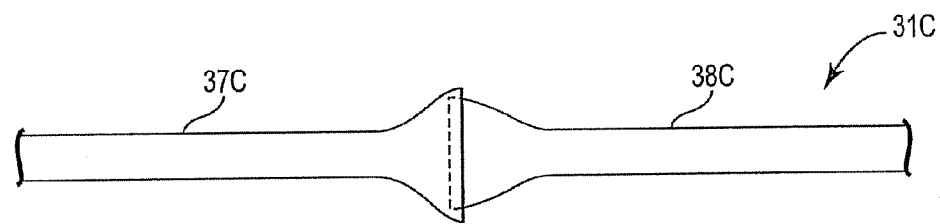
Figure 9D:
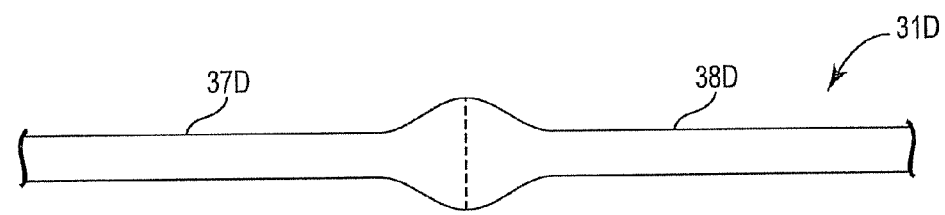

FIG. 9A-9D illustrate various embodiments of removable sheath members 31 structured to cover at least a portion of a sling, such as sling 16, in order to promote passage of the sling through the tissues during the surgical placement. Particularly, FIG. 9A is a first exemplary embodiment of a sheath 31A that includes a first elongated sleeve member 37A and a second elongated sleeve member 38A. As illustrated in FIG. 9A, elongated sleeve members 37A and 38A are each structured to receive one of the arms of the sling therein. Next, FIG. 9B is a second exemplary embodiment of a sheath 31B that also includes a first elongated sleeve member 37B and a second elongated sleeve member 38B. However, unlike sheath 31A, the first and second elongated sleeve members 37B and 38B of sheath 31B are each structured to receive a part of the central portion of the sling. Furthermore, the first and second elongated sleeve members 37B and 38B are structured such that their ends abut one another to create a seam near the center of the sling. The ends of the first and second elongated sleeve members 37B and 38B may be joined using any suitable connection method, such as within an adhesive. In another embodiment, there is a "score" line between the first and second elongated sleeve members 37B and 38B. Alternatively, the ends are not joined, but are rather freely positioned adjacent one another. Moving on, FIG. 9C is a third exemplary embodiment of a sheath 31C that includes a first elongated sleeve member 37C and a second elongated sleeve member 38C that are each structured to receive part of the central portion of the sling. Unlike the first and second elongated sleeve members 37B and 38B of sheath 31B, the first and second sleeve members 37C and 38C overlap one another as shown in FIG. 9C. Finally, FIG. 9D is a fourth embodiment of a sheath 31D that includes a first elongated sleeve member 37D and a second elongated sleeve member 38D that are each structured to receive a part of the central portion of the sling. As will be appreciated by those skilled in the art, sheath 31D is similar to sheath 31B previously described. However, the first and second elongated elements 37D and 38D of sheath 31D have a perforated connection.

FIGS. 10-12 demonstrate the use of an alternative needle introducer 27 that may be placed, for example, from the medial thigh to the incision beneath the rectum as previously described. Once through the tissue, a jaw element of the needle introducer 27 opens in the middle, which reveals a grasping instrument 28 that can hold on to a suture, such as suture 33 of sling arm 17. As illustrated in FIG. 13, the sling aim 17 may have a plastic sheath 31 positioned thereon. The sling arm 17 may then be brought through the tissue, with or without the use of an outer tube 26 through which the grasping instrument 28 had been placed during the needle insertion process.

FIGS. 13-15 demonstrate the use of another alternative needle introducer 32 that, after insertion through the tissue, can be advanced beyond an outer tube 26, with or without a spring-mechanism to deploy the needle. When the needle introducer 32 is advance, a notch 30 may be revealed upon which the suture loop 33 (previously attached to the mesh) can be placed. The sling arm 17 may then be brought up through the tissues to the medial thigh as previously described.

FIGS. 16-18 demonstrate the use of yet another alternative needle introducer 34 that, after insertion through the tissue, may be separated from a shaft 35 of the needle by unscrewing the needle tip. The sling may be designed with a male-connector screw 36 that attaches to the straight needle shaft 35 prior to withdrawing the needle shaft 35, which in turn draws the mesh sling arm 17 up through the tissue.

Figure 19:
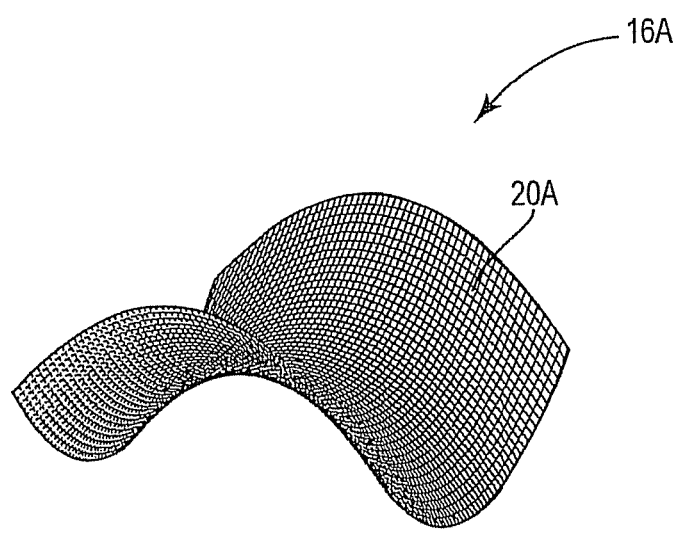
FIG. 19 is a diagram illustrating an alternative sling embodiment having a center portion with a generally curved, saddle-like shape.
Figure 20:
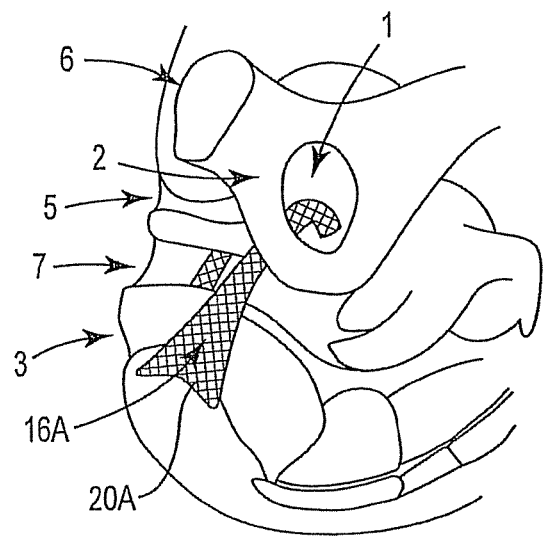
FIGS. 20-21 illustrate exemplary positioning of the sling of FIG. 19 within a patient.
Figure 21:
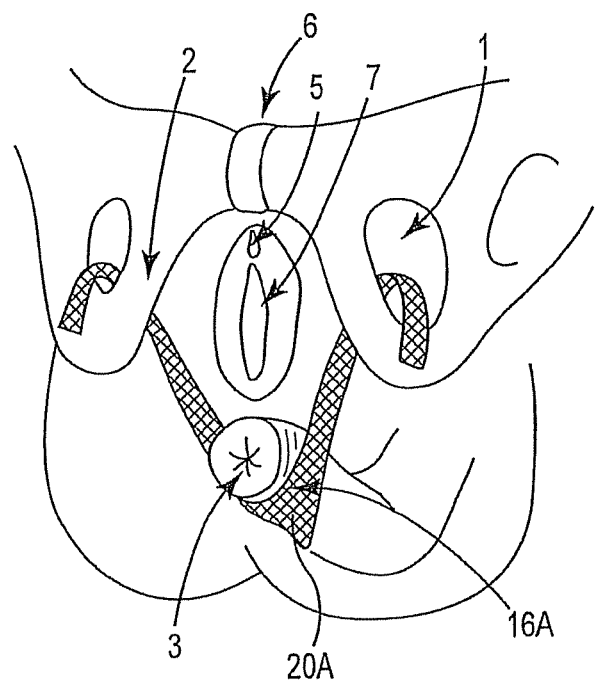

Now that one exemplary embodiment of a sling has been described, along with a method of placing the sling and devices for assisting in such placement, several alternative sling embodiments will be described. Particularly, FIG. 19 is a diagram illustrating a sling 16A having a center portion 20A (arms not shown) with a generally curved, saddle-like shape. As will be appreciated by those skilled in the art, the saddle shape may facilitate making good contact with the anatomy to be supported. FIGS. 20-21 illustrate exemplary positioning of the sling 20A in accordance with the present invention. As shown in FIGS. 20-21, one curve of the saddle allows the sling to arc between the obturator regions, while the other curve can complement the ano-rectal angle.

Figure 22:
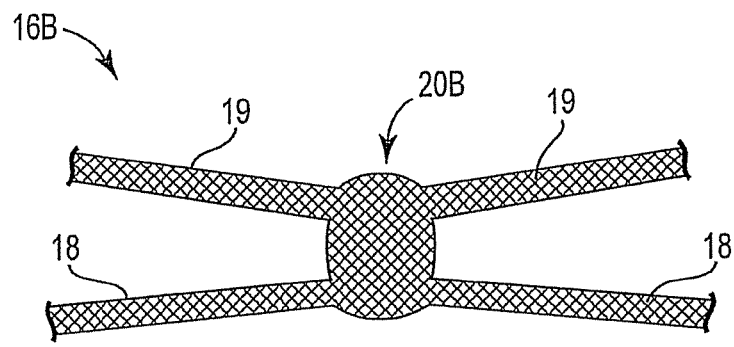
FIG. 22 depicts an alternative sling embodiment having four sling alms.

FIG. 22 is a diagram illustrating sling 16B, which is a second alternative sling embodiment in accordance with the present invention. As shown in FIG. 22, sling 16B includes a center portion 20B with four attached arms, namely a first pair or arms 18 and a second pair of anus 19. The aims 18 may be structured to be passed from the medial superior portion of the obturator membrane, and the arms 19 may be structured to be passed through the inferior portion of the obturator membrane.

Figure 23A:
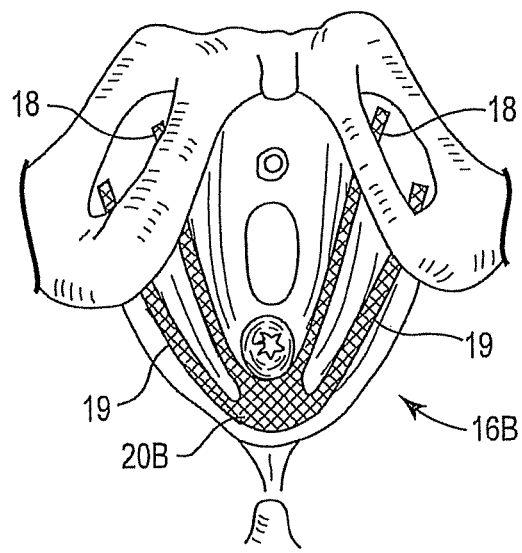
FIGS. 23A-23B are diagrams illustrating one exemplary positioning of the sling of FIG. 22 within a patient.

FIG. 23A is a diagram illustrating one exemplary positioning of the sling 16B in accordance with the present invention. Particularly, FIG. 23A demonstrates the use of two pairs of synthetic mesh straps placed through the obturator membrane, the first pair 18 more distal and placed near the superior-medial aspect of the obturator foramen, and the second pair 19 placed near the inferior portion of the obturator foramen.

Figure 23B:
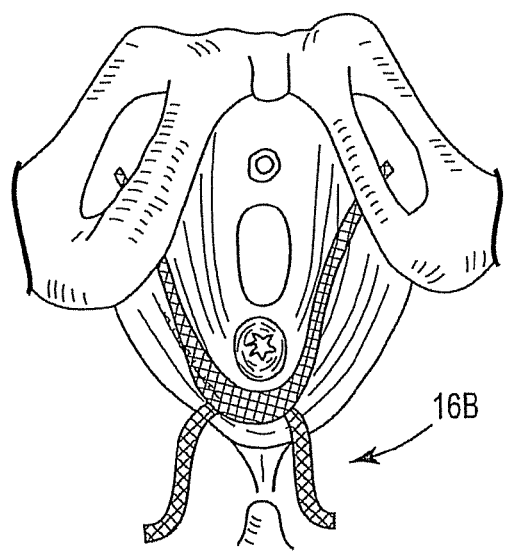

FIG. 23B is a diagram illustrating another exemplary positioning of the sling 16B in accordance with the present invention. Particularly, FIG. 23B demonstrates the positioning of one of the pairs of arms such that they are secured in place by passage into subcutaneous tissue in order to prevent rolling of the sling. The pair or arms may be directed posteriorly, on either side of the coccyx, in order to keep the subrectal portion flat.

Figure 24:
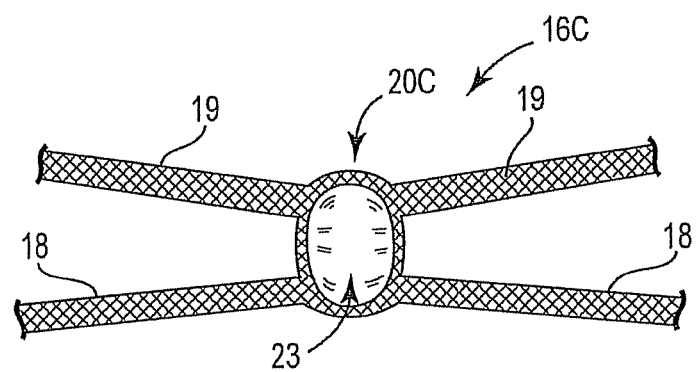

FIGS. 24-29 illustrate various sling embodiments having fluid-filled sacs coupled thereto. FIG. 24 is a diagram illustrating sling 16C, which is a third alternative sling embodiment in accordance with the present invention. Particularly, FIG. 24 illustrates a superior view of the sling 16C having a fluid-filled sac 23 on the superior side of the central portion 20C of the sling. Although the sling 16C of FIG. 24 illustrates two pairs of arms extending from each end of the central portion 20C, those skilled in the art will appreciate that the use of fluid-filled sacs is not dependent upon the number of sling aims. Therefore, slings having any number of aims may include a fluid-filled sac without departing from the intended scope of the present invention.

Figure 25:
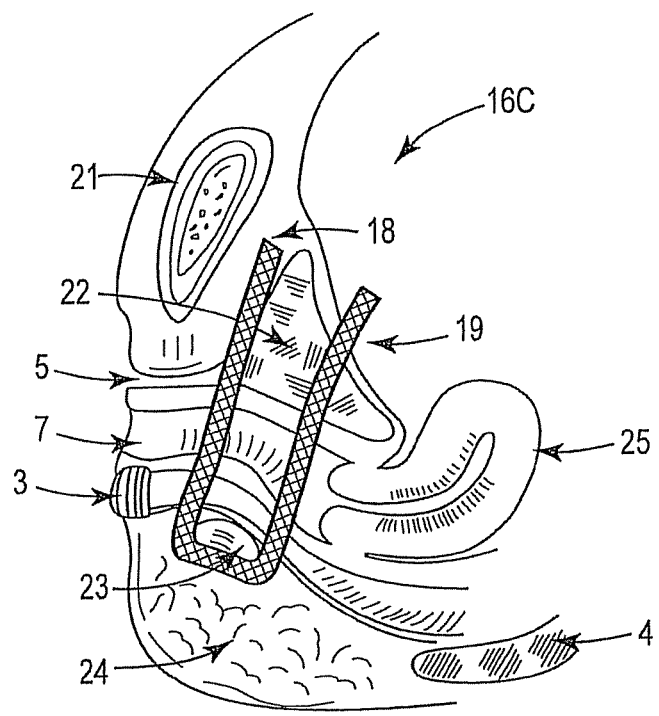

FIG. 25 shows a lateral orientation of the pelvis and the sling 16C with the pubic symphysis 21, the bladder 22, the uterus 25, and the ischiorectal fossa 24 with two synthetic straps (i.e., first pair 18 and second pair 19) on each side. As illustrated in FIG. 25, the fluid-filled sac 23 is positioned in a sub-rectal location.

Figure 26:
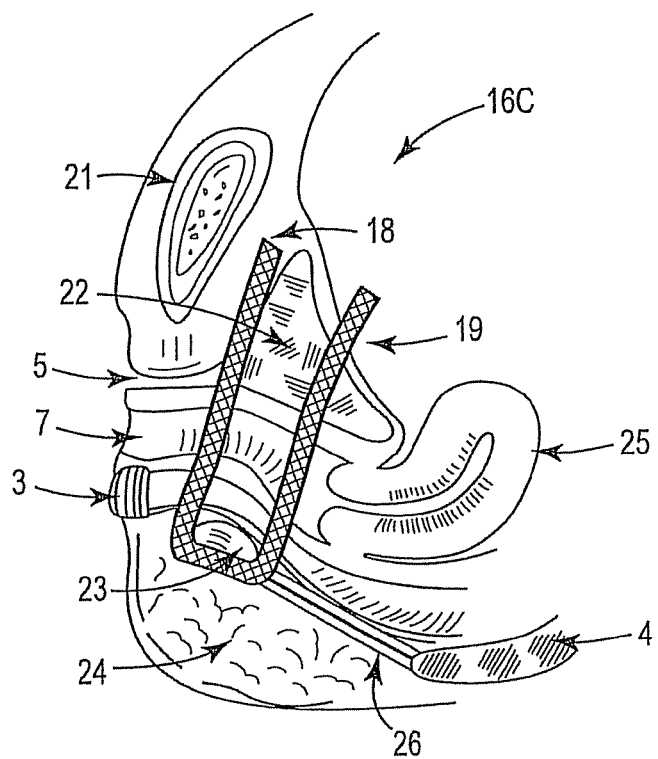

FIG. 26 is a diagram similar to FIG. 25 showing a lateral orientation of the pelvis with the sling 16C in place. However, as illustrated in FIG. 26, sling 16C further includes an extension 26 of the sub-rectal element attached to the coccyx. As will be appreciated by those skilled in the art, the extension 26 may be attached to the coccyx with numerous elements including, but not limited to, sutures, bone anchors, or other suitable methods of affixing synthetic material to the coccyx.

FIG. 27 is a diagram illustrating sling 16D, which is a fourth alternative sling embodiment in accordance with the present invention that also includes a central portion 20D with an inflatable, fluid-filled sac 47. As shown in FIG. 27, connector tubing 48 is attached to the fluid-filled sac 47 and can be placed under the buttocks or other location within the reach of the tubing. Additionally, the fluid-filled sac 47 has a port 39 at the end that can be used for filling or reducing the amount of fluid that is contained within the sac 47.

FIG. 28 is a diagram illustrating an inferior view of a sling 16E, which is a fifth alternative sling embodiment in accordance with the present invention. The sling 16E includes a fluid-filled sac 49 having a port 40 accessible through an aperture at the bottom of the central portion 20E of the sling. As will be appreciated by those skilled in the art, the port 40 may be accessed subcutaneously in order to either add more fluid or remove fluid.

Figure 29:
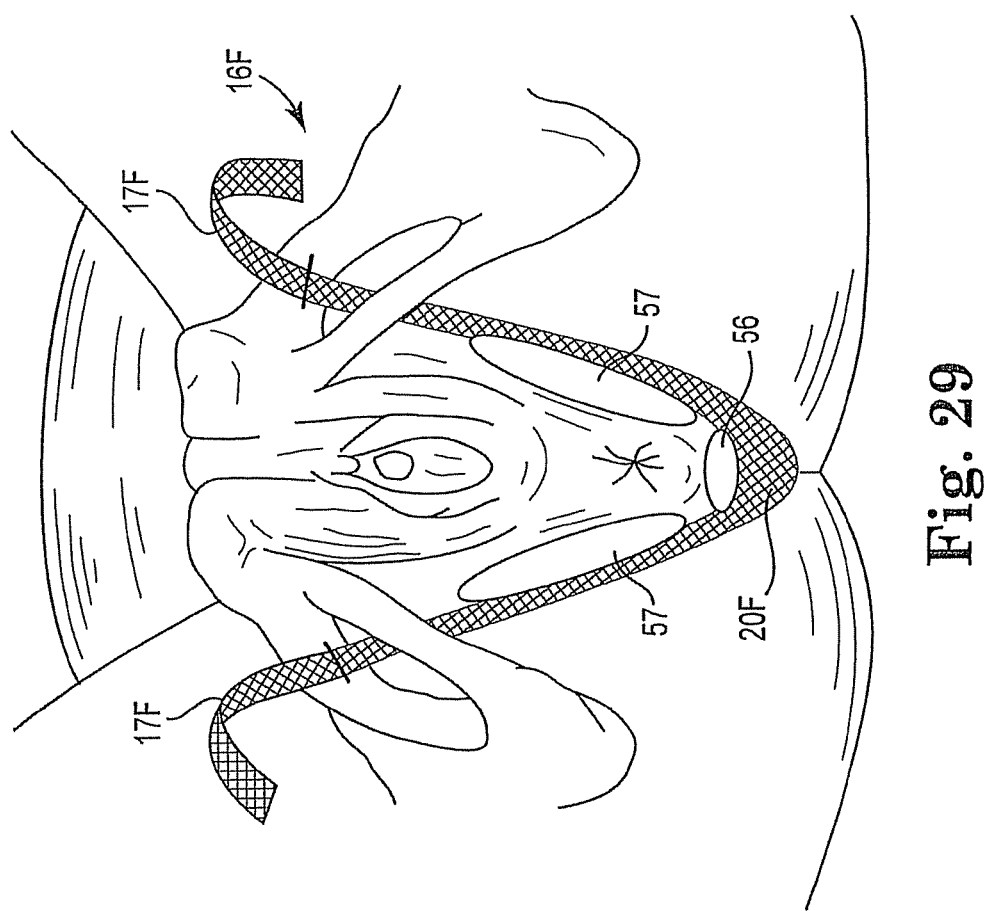

FIG. 29 is a diagram illustrating a sling 16F positioned within a patient. The sling 16F is another alternative embodiment of a sling in accordance with the present invention and generally includes a first fluid-filled sac 56 superior to the central portion 20F of the sling, along with a pair of inflatable sacs 57 positioned medial to the aims 17F of the sling. It follows that fluid-filled sacs may be positioned adjacent areas other than the central portion of the sling without departing from the intended scope of the present invention.

As will be appreciated by those skilled in the art based on the foregoing, the fluid filled sacs of the present invention may be used for either intra or post operative sling adjustment. Adjustment may be made by, for example, a connector tube having a port attached thereto, or via a subcutaneous access port that controls one or more of the fluid-filled sacs. As previously discussed, "fluid" should be understood to include gasses, liquids, and semisolid media (such as gels).

For example, the fluid-filled sacs may be structured in the form of inflatable balloon elements that may be filled with air or other gasses.

FIGS. 30-33 exhibit an exemplary use of a loop stylet during the placement of a sling in accordance with the present invention. As shown in FIGS. 30-33, stylet 41 may be advanced through a tube 42 positioned within the patient along the desired path of a sling arm. A length of sling material 43 may be threaded through a loop on an end of the stylet 41 so that the material catches in the loop. The stylet may then be withdrawn back through the tube 42 to bring the end of the sling material 43 to the desired position.

Figure 34:
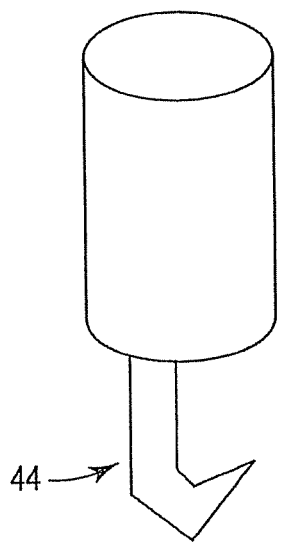
FIGS. 34-35 depict an exemplary use of a stylet having a hook.
Figure 35:
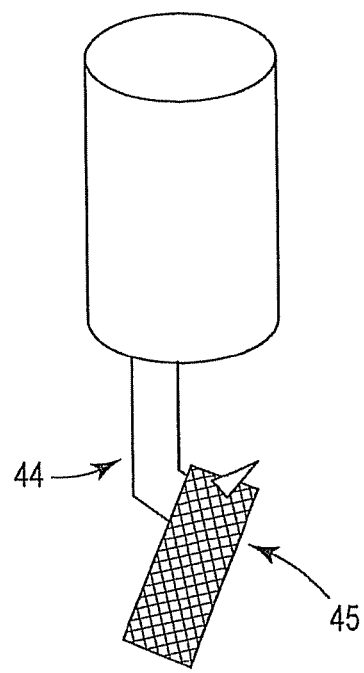

Alternatively, FIGS. 34-35 show an exemplary use of a hook stylet 44 during the placement of a sling in accordance with the present invention. As shown in FIGS. 34-35, a piece of sling material 45 may be stabbed onto a sharp tip of the hook 44. The hook 44 may then be withdrawn through a tube, such as tube 42 in FIGS. 30-33, to bring the end of the sling material 45 to the desired location.

Figure 36:
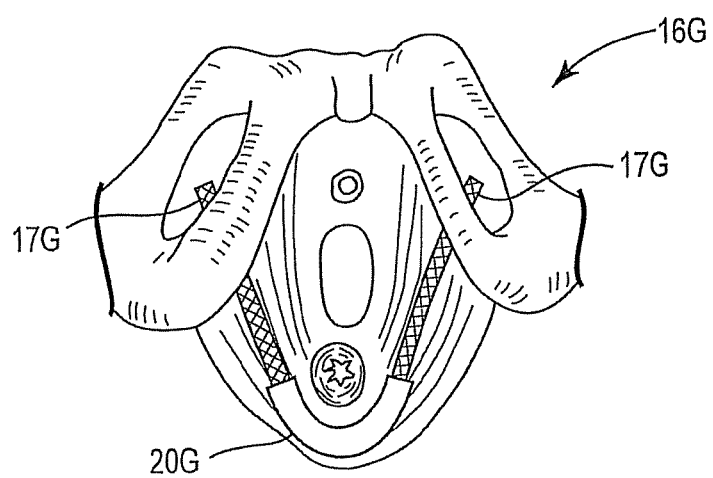
FIG. 36 depicts one exemplary embodiment of a hybrid sling in accordance with the present invention.

FIG. 36 is a diagram illustrating a hybrid sling 16G in accordance with the present invention. Particularly, the hybrid sling 16G may be comprised of, for instance, synthetic mesh arms 17G attached to a natural material forming the center portion 20G placed under and/or lateral to the ano-rectum.

Figure 37A:
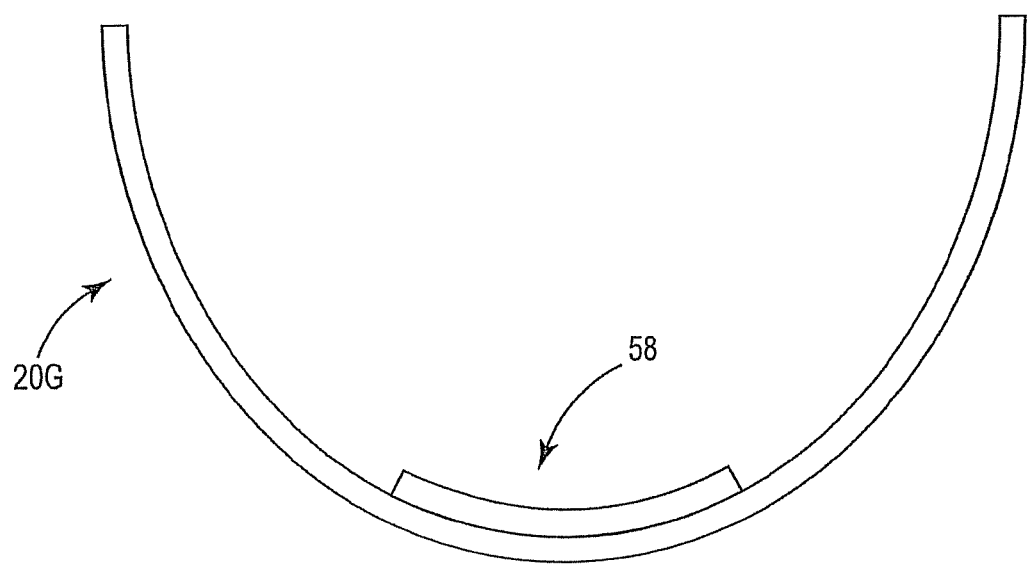
FIGS. 37A-37C depict alternative embodiments of hybrid slings in accordance with the present invention.
Figure 37B:
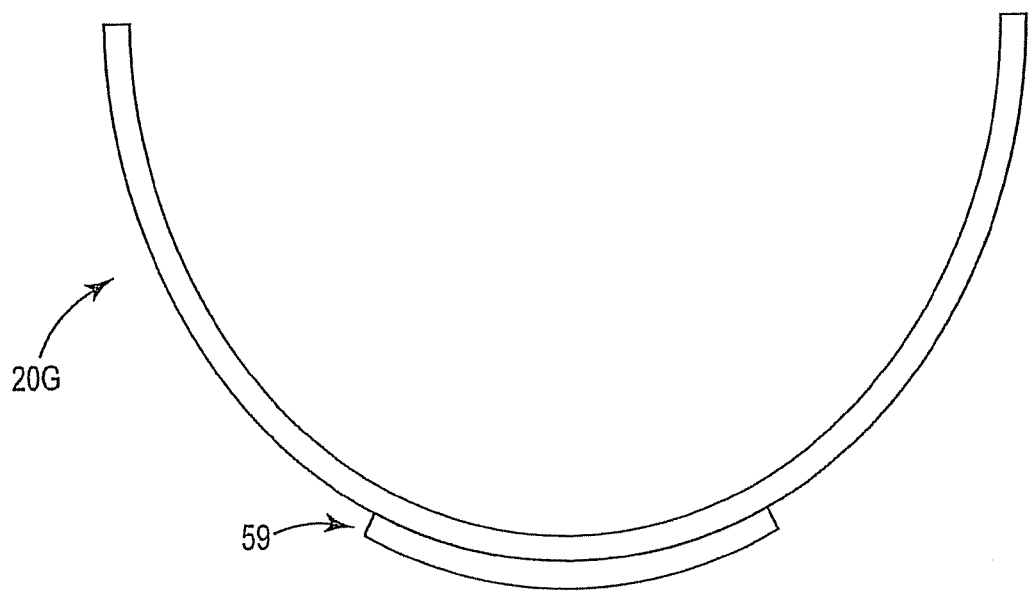
Figure 37C:
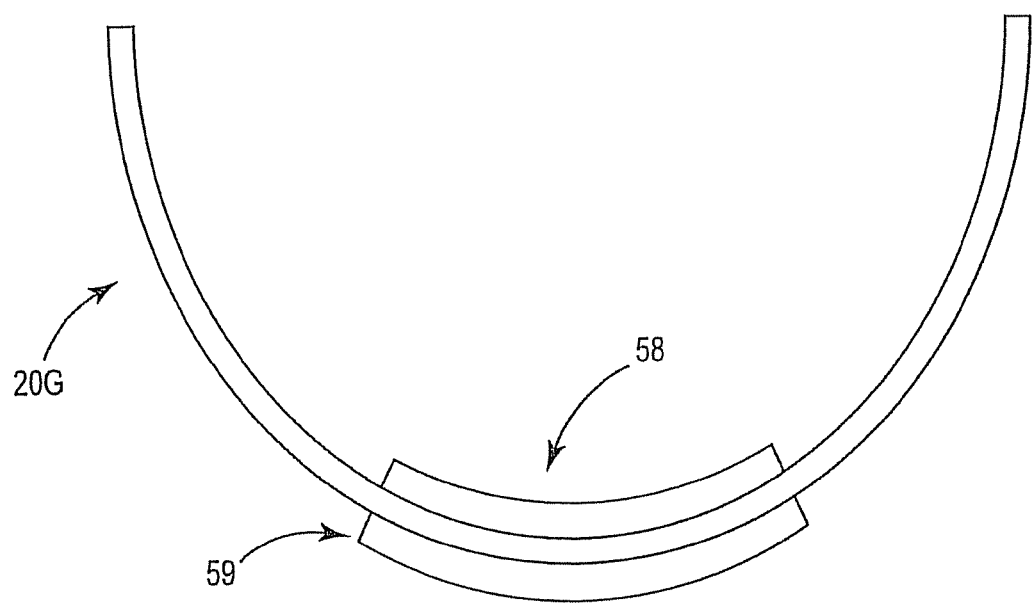

Alternative hybrid sling configurations are illustrated in FIGS. 37A-37C. Particularly, FIG. 37A is a cross-sectional view of the center portion 20G of sling 16G having a natural graft 58 positioned on a superior surface of the synthetic sling. FIG. 37B is a cross-sectional view of the center portion 20G of the sling 16G having a natural graft 59 positioned on an inferior surface of the synthetic sling. Finally, FIG. 37C is a combination of the slings of FIGS. 37A and 37B that includes natural grafts 58 and 59 positioned on both superior and inferior surfaces of the synthetic sling, respectively. Although not shown, other alternative sling embodiments may include a natural graft that is attached to one or both of the sling arms in addition to, or instead of, the central portion of the sling. As will be appreciated by those skilled in the art, attaching a natural graft to the central portion and/or the aims of a sling may reduce the risk of erosion of the sling into either the rectum or the overlying skin.

Figure 38A:
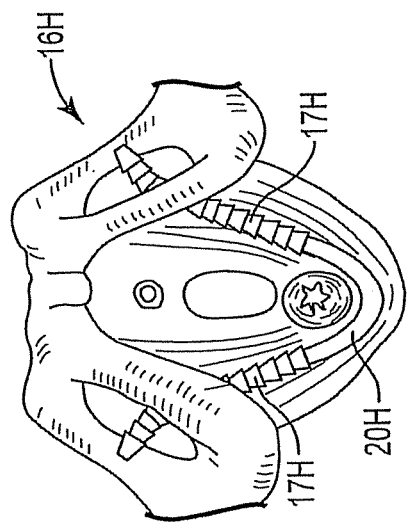
FIGS. 38A-38B illustrate another exemplary sling positioned within a patient that includes sling arms having serrations.
Figure 38B:
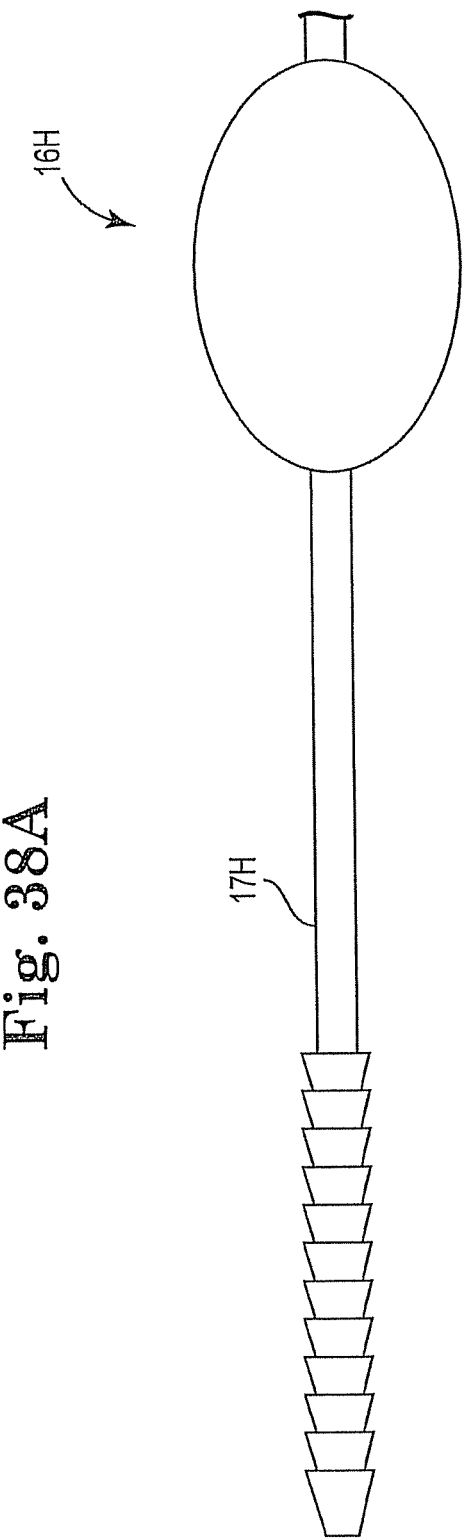

FIGS. 38A-38B illustrate another exemplary sling 16H positioned within the patient that includes sling arms 17H made of a non-mesh, synthetic material with serrations on each arm that maintain the sling in position after adjustment by the surgeon. Suitable synthetic materials may include, but are not limited to, silastic, polypropylene, or other suitable plastics.

Figure 39:
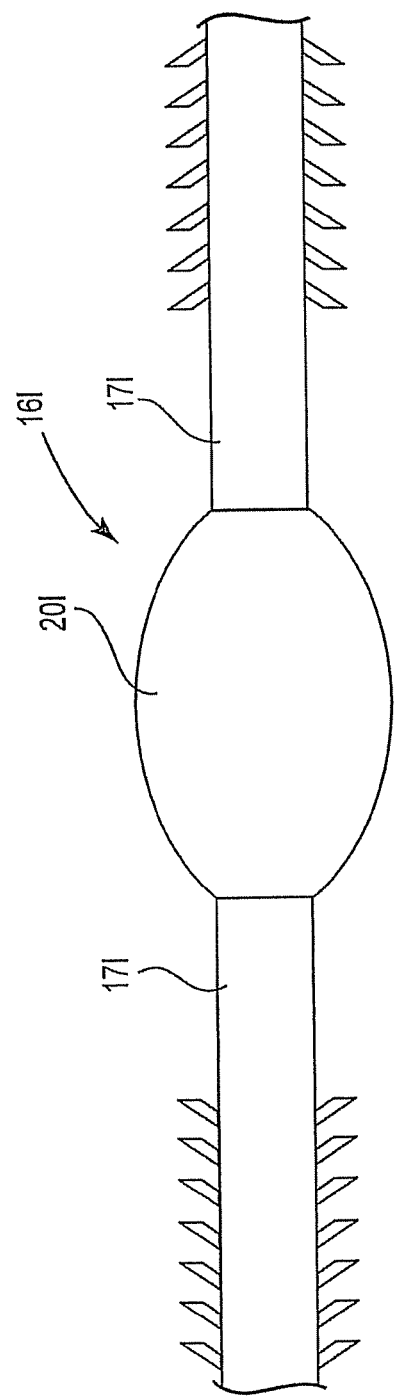
FIG. 39 depicts one exemplary sling embodiment having aims that include a plurality of tines.

FIG. 39 illustrates an alternative sling 161 similar to the sling 16H of FIGS. 38A-38B, but instead including a plurality of tines rather than serrations on the arms 171. However, as will be appreciated by those skilled in the art, the tines may serve the similar function of maintaining the sling in position by grasping onto tissue.

Figure 40:
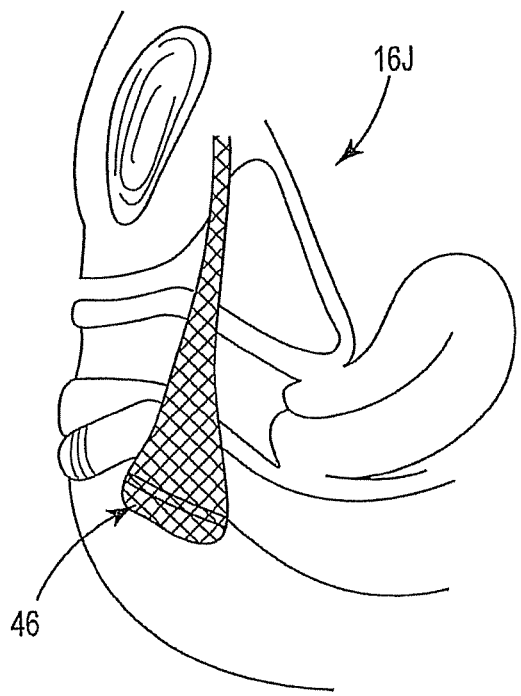
FIGS. 40-42 illustrate one exemplary embodiment of a sling that includes rigid or semi-rigid elements coupled to a central portion thereof.
Figure 41:
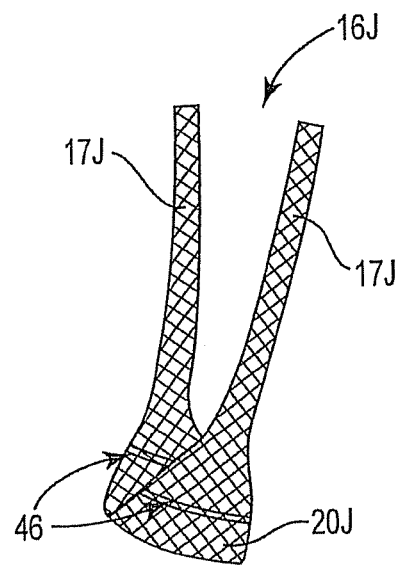
Figure 42:
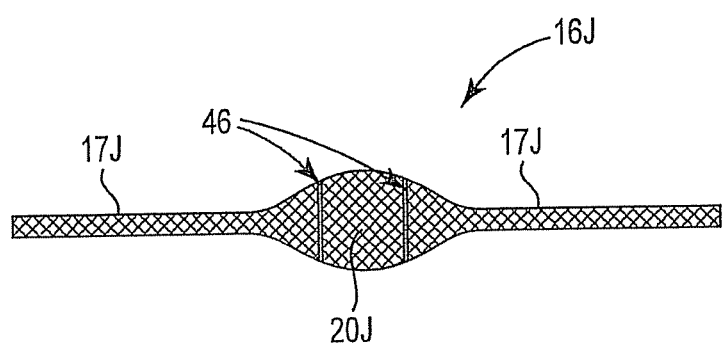

FIGS. 40-42 illustrate one exemplary embodiment of a sling 16J that includes rigid or semi-rigid elements 46 coupled to the central portion 20J of the sling. The elements 46 may be attached to the sling 16J in order to keep the sling from rolling under the ano-rectal portion. As will be appreciated by those skilled in the art, the elements 46 may comprise synthetic or natural elements that are attached to the mesh in a direction transverse to the length of the sling, such as perpendicular or substantially perpendicular to the length of the sling. The elements 46 may be semi-rigid and may be so positioned in the mesh as to be located under or lateral to the bowel when the mesh is deployed, for the purpose of keeping the mesh from rolling up underneath the ano-rectum. For example, the elements 46 may comprise stiff or flexible bars coupled to the sling such that they are located on either side of the rectum, and may be structured to prevent rolling of the sling material.

Figure 43:
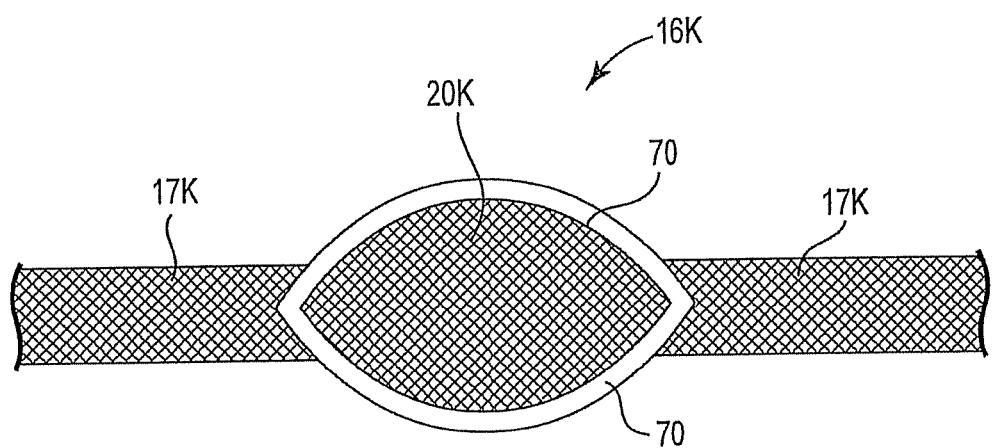
FIG. 43 illustrates another exemplary embodiment of a sling that also includes rigid or semi-rigid elements coupled to a center portion thereof.

FIG. 43 illustrates a sling 16K that also includes rigid or semi-rigid elements coupled to the center portion 20K of the sling. Particularly, sling 16K includes a plurality of struts 70 adjacent outer edges thereof. The struts 70 may be fixated from any suitable biocompatible material, such as a plastic, and may be structured to be folded inward for passage into an area beneath the ano-rectum. Once the central portion 20K of the sling 16K is positioned at the desired location within the patient, the folded central portion of the sling may "spring" open into position due to the presence of the struts 70, thereby allowing the central portion 20K of the sling 16K to lie flat under the ano-rectum.

Figure 44A:
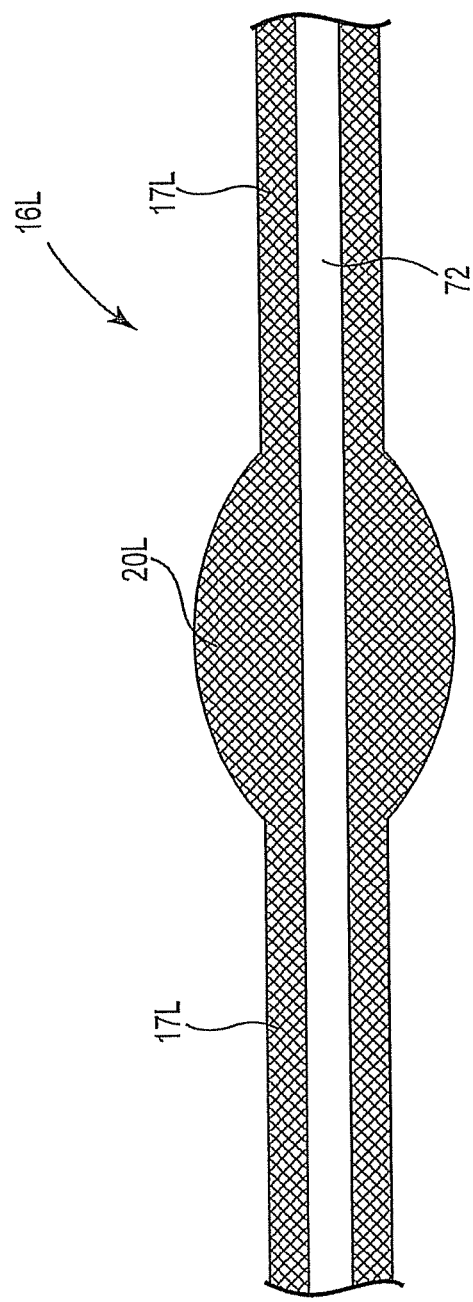

FIGS. 44A-44B demonstrate alternative sling embodiments illustrating the use of "less elastic" sections of material in one or more areas of the sling. Particularly, FIG. 44A is a diagram illustrating a mesh sling 16L with a strip of material 72 that runs substantially the entire length of the sling, wherein the mesh portion of the sling has an elasticity that is greater than the strip of material 72 extending along the sling. In one exemplary embodiment, the less elastic material may be a polypropylene ribbon material disposed within or extending along an outer surface of the sling 16L, although any suitable material having an elasticity less than that of the sling material may be used without departing from the intended scope of the present invention. Similarly, FIG. 44B is a diagram illustrating a mesh sling 16M with a pair of material strips 74 running substantially along the entire length of the sling arms 17M, but not within the central portion 20M of the sling. Once again the material strips 74 may be any suitable material having an elasticity less than that of the sling material. As will be appreciated by those skilled in the art, adding a stiffer material to the mesh aims and/or central portion of the sling may increase the ability to apply greater tension on the sling, if necessary.

Figure 45:
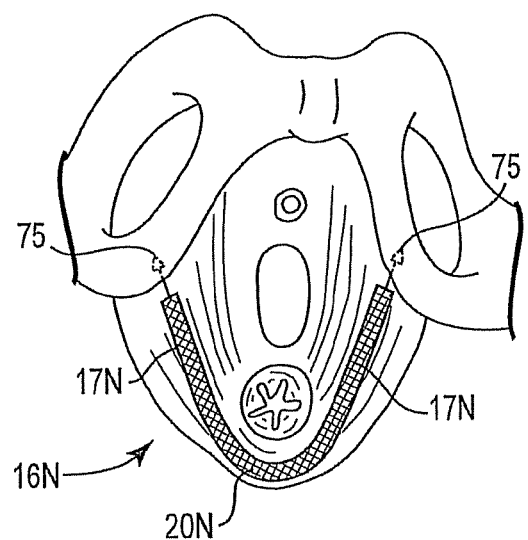
FIG. 45 is a diagram illustrating an exemplary sling embodiment having arms that are anchored to the inferior-medial portion of the ischiopubic rami with bone anchors.

FIG. 45 is a diagram illustrating a sling 16N positioned within the patient and having sling arms 17N that extend to the inferior-medial portion of the ischiopubic rami and are anchored thereto with bone anchors 75 in order to hold the sling into position.

Figure 46:
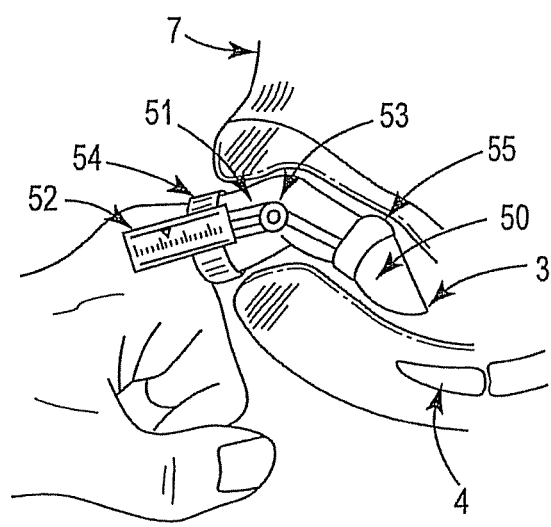
FIG. 46 depicts the use of an exemplary device to measure the ano-rectal angle.

FIG. 46 depicts a device attached to the examiner's finger used to measure the angle between the rectum 3 and anus. The vagina 7 rests anterior to the anus and rectum, and the coccyx 4 is located posterior to the rectum. A proximal ring 54 is placed on the proximal phalanx 51 and the distal ring 55 is placed on the distal phalanx 50 and these are connected by a joint 53. The angle made between the anus and rectum is measured and displayed on a visual scale 52.

In one exemplary embodiment, a method to treat anal incontinence and/or defecatory dysfunction in a male or female may include:

placing an implant that passes under the anus and/or rectum and may pass under, over, or through the levator ani muscles;

placing one of the ends of the implant through the obturator foramen and through an incision made in the medial thigh on the same side of the patient; and providing an elongate instrument that is used to transfer one end of the implant from the post-anal incision to a medial thigh incision, and then transferring the other end of the implant from the post-anal incision to the other medial thigh incision; or providing an elongate instrument that is used to transfer one end of the implant from a medial thigh incision to the post-anal incision, and then transferring the other end of the implant from the other medial thigh incision to the post-anal incision.

In another exemplary embodiment, a method of treating anal incontinence and/or defecatory dysfunction in a male or female patient may include:

creating an incision between the anus and the coccyx (vertical or horizontal);

creating an incision in the medial portion of each thigh;

providing an elongate instrument and an elongate implant for treating the condition;

passing one of the ends of the instrument between the post-anal incision, through an obturator foramen on one side of the patient, and the incision on the respective medial thigh;

associating the implant with the instrument;

using the instrument to pass the implant through the tissue between the postanal incision and one thigh incision such that the implant extends between the postanal incision, through the one obturator foramen, and one of the thigh incisions;

passing one of the ends of the same or another instrument between the postanal incision, through the other obturator foramen, and the other thigh incision; and using the instrument to extend the implant between the post-anal incision, through the other obturator foramen, to the other thigh incision such that the implant then extends from one thigh incision to the other thigh incision, through both obturator foramen and under the patient's rectum and/or anus (below or above the level of the levator ani muscles).

Various embodiments disclosed herein can be combined with one another to provide additional embodiments that include multiple features.

Figure 47:
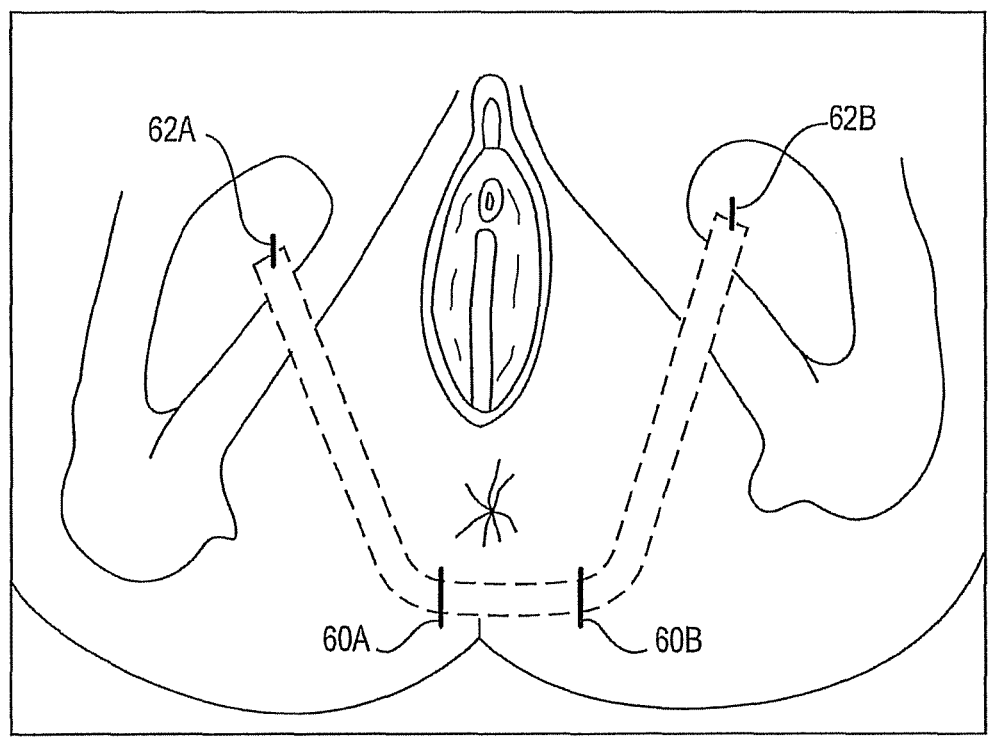
FIG. 47 generally depicts another exemplary method for treating anal incontinence, defecatory dysfunction, or pelvic organ prolapse according to the present invention.

In another aspect of the present invention, the various slings and insertion needles described above in reference to the treatment of anal incontinence, defecatory dysfunction, or pelvic organ prolapse may be used in conjunction with another method for treating these conditions. In particular, FIG. 47 generally depicts one exemplary method for treating anal incontinence, defecatory dysfunction, or pelvic organ prolapse according to the present invention. The method begins at step 1 where a physician marks the location of four incisions on a patient's pelvic region. In particular, the physician marks two posterior buttock incisions 60A and 60B and two thigh incisions 62A and 62B. The posterior incisions 60A and 60B may be located about 1.5 cm lateral and about 3 cm posterior to the mid-anus (midway between the anus and the coccyx). The two thigh incisions 62A and 62B may be, for example, at the level of the urethra along the descending pubic ramus.

The method continues at step 2 where the physician may inject a local anesthetic along a track from each thigh incision to the corresponding post-anal incision on the ipsilateral side, and between the two post-anal incisions. Then, in step 3, the physician uses a scalpel to make the two posterior incisions 60A and 60B, which may be approximately 1.5 cm in length. Next, in step 4, a small curved Kelly clamp or similar instrument may be used to tunnel subcutaneously between the two posterior incisions 60A and 60B to create a space between the incisions, posterior to the anus. The physician may place a finger in the rectum to assist in guiding the clamp during the tunneling process. The method continues at step 5 where the physician inserts the clamp into posterior incision 60B and through posterior incision 60A, grasping an end portion of a sling aim or a connector on the sling. Thereafter, the physician pulls the sling through both incisions 60A and 60B until the central portion of the sling lies beneath the ano-rectum.

Then, in step 6, the physician makes a small stab incision over a first one of the thigh incision marks to create thigh incision 62A. An insertion needle (such as, for example, needle 11) is then inserted through thigh incision 62A in step 7 until it perforates the obturator membrane. The needle is tracked around the ischiopubic ramus with the handle portion of the needle generally parallel to the pelvic floor. The physician may use a finger to track the path of the needle down next to the vagina. Next, in step 8, the physician moves his finger to posterior incision 60A to track the needle out of the incision. The procedure continues at step 9 where the physician attaches the needle to the connector on the end of the sling arm protruding outward from posterior incision 60A and withdraws the needle back through the tissue and out through thigh incision 62A, pulling the sling arm to the desired location.

Next, in step 10, the physician makes a small stab incision over the second thigh incision mark to create thigh incision 62B. The insertion needle is then inserted through thigh incision 62B in step 11 until it perforates the obturator membrane. The needle is again tracked around the ischiopubic ramus with the handle portion of the needle generally parallel to the pelvic floor. Thereafter, in step 12, the physician moves his finger to posterior incision 60B to track the needle out of the incision. The procedure continues at step 13 where the physician attaches the needle to the connector on the end of the sling arm protruding outward from posterior incision 60B and withdraws the needle back through the tissue and out through thigh incision 62B, pulling the sling arm to the desired location. Once the physician has grasped and pulled both of the sling aims through the corresponding thigh incisions 62A and 62B, posterior incisions 60A and 60B may then be irrigated with an antibiotic solution and sutured in step 14.

Next, with a finger inserted into the rectum, the physician adjusts the sling arms in step 15 by grasping the excess portions of the aims protruding from thigh incisions 62A and 62B and pulling upward on both aims until gentle tension is palpable through the rectum. Then, keeping a finger in the rectum, the physician cuts the sling aims (as well as the sheath, if present) from the insertion needles and the sheaths are removed, leaving the sling mesh in place. The sling arms are then cut close to the patient's skin such that any excess portions of the sling aims protruding outward from the thigh incisions 62A and 62B are removed. The thigh incisions 62A and 62B are then irrigated with an antibiotic solution and subsequently sutured in step 16, thereby completing the sling implantation procedure. The sling, which may be constructed as a mesh formed from many materials such as, for example, polypropylene, adheres to internal body tissue without the need for additional sutures or attachment means.

One skilled in the art will appreciate that the procedure described above is merely one example of an alternative method for treating anal incontinence, defecatory dysfunction, or pelvic organ prolapse according to the present invention. Thus, the steps described above may be modified or re-ordered without departing from the intended scope of the present invention. Furthermore, although the method was described with reference to the treatment of pelvic organ prolapse in a female patient, those skilled in the art will appreciate that a similar method may be used to treat pelvic organ prolapse in a male patient as well. In addition, insertion needles and slings other than those shown and described above in reference to FIGS. 2-46 may be used along with the method of the present invention. To that end, additional devices and sling features that may be especially useful in the alternative method depicted in FIG. 47 will be described below.

When grasping one of the arms of a sling with a clamp or similar device and pulling it through the subcutaneous tunnel from one buttock incision to the other buttock incision, the clamp may occasionally lose its grip on the sling arm. As a result, the physician must find the end of the sling aim and try to re-clamp the arm before continuing the procedure. In order to eliminate this type of scenario, sling arms may be designed with a connector that may be reversibly attached to a transfer device to allow for improved transfer from one buttock incision to the other. This transfer device could be reversibly attached to the connector via any suitable means including, but not limited to, extendable tines, wings, or an inflatable balloon, which would allow the device to release the connector once the transfer from one buttock incision to the other buttock incision on the opposite side is complete. Control of the connecting means on the transfer device may be accomplished with any suitable actuator including, but not limited to, a push-button type actuator or the like.

Figure 48A:
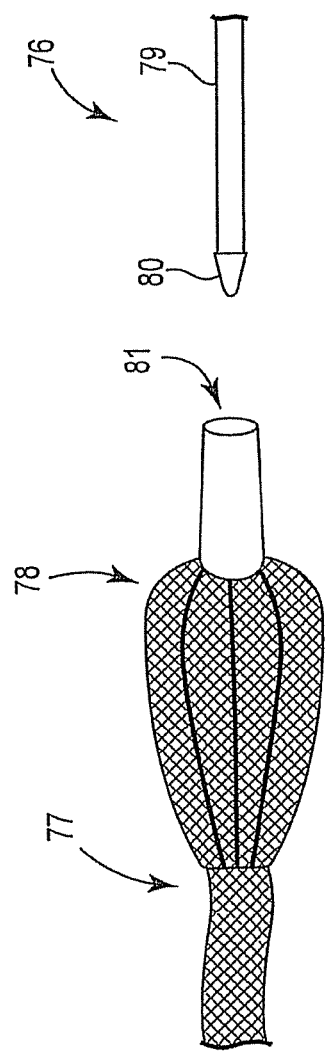
FIGS. 48A-48B depict an exemplary transfer device that can be used to reversibly connect to connectors attached to sling aims to allow for transfer from one buttock incision to another buttock incision.
Figure 48B:
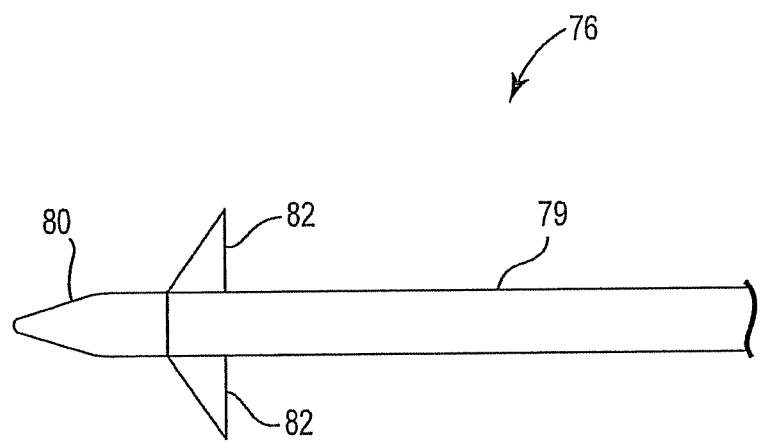

FIGS. 48A-48B depict the use of one exemplary transfer device 76 in accordance with the present invention. Particularly, FIG. 48A illustrates a portion of a sling arm 77 having a connector 78 extending from an end thereof. The transfer device 76 generally includes an elongate body 79 and a tip 80 structured for insertion within an aperture 81 in a distal end of the connector 78. Upon insertion into the aperture 81, one or more wings 82 may extend from the elongate body 79 of the transfer device 76 as illustrated in FIG. 48B. In this extended position within aperture 81, the connector 78 is reversibly coupled to the transfer device 76 and the sling arm 77 may be pulled through the tunnel from one buttock incision to the other buttock incision. Once the sling 77 has been pulled through the tunnel, the wings 82 may be moved back to a retracted position thereby releasing the connector 78 from the transfer device 76.

Those skilled in the art will appreciate that transfer device 76 is presented merely for purposes of example and not limitation. Thus, numerous other types and styles of transfer devices may be used without departing from the intended scope of the present invention.

As will be appreciated by those skilled in the art, transferring of the sling from the first incision 60A to the second incision 60B (or vice versa) may be improved with the addition of a plastic sheath that covers the arms and/or central portion of the sling body. Exemplary sheaths were previously illustrated in FIGS. 9A-9D. However, any suitable sheath embodiment may be used without departing from the intended scope of the present invention.

Figure 50:
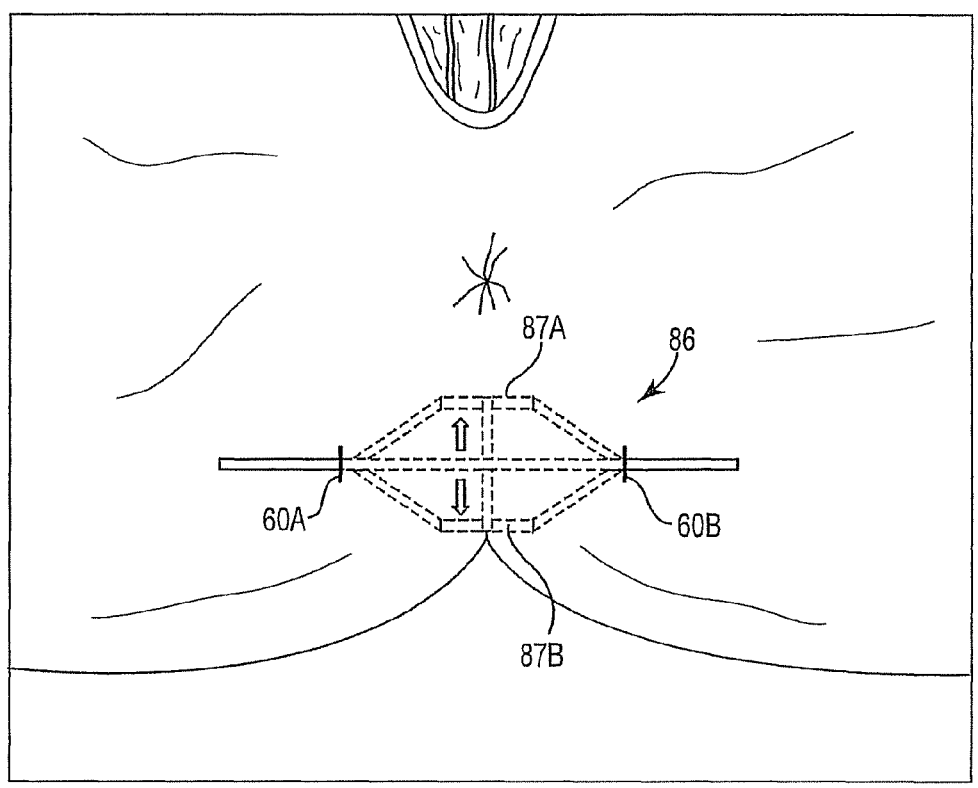
FIG. 50 demonstrates the tunneling device of FIG. 49 in place between two buttock incisions.
Figure 51:
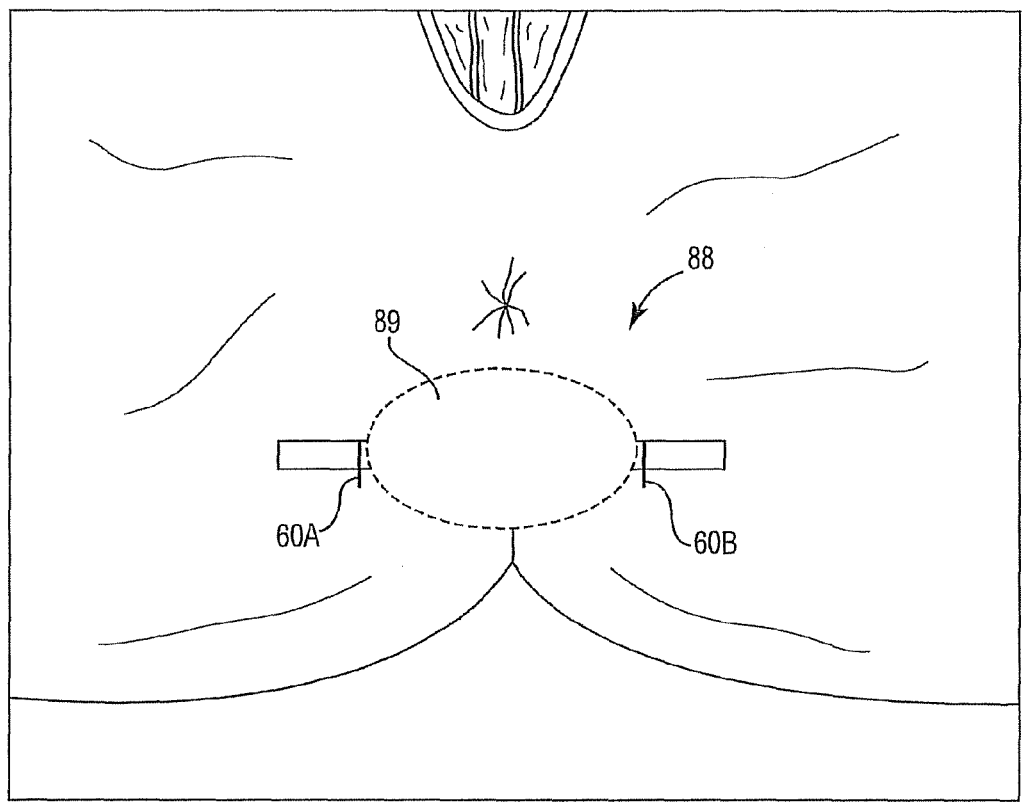
FIG. 51 demonstrates a balloon device that can be used to tunnel between two buttock incisions and then be inflated to dilate the path.

In order to further assist the surgeon in transferring a sling arm between the first incision 60A and the second incision 60B, a tunneling device may be use to widen the path between the two incisions. Widening the path may also help the sling lie flat under the ano-rectum. FIGS. 49-51 illustrate various exemplary embodiments of tunneling devices that may be used to widen the path between the incisions 60A and 60B in accordance with the present invention.

Particularly, FIG. 49 is diagram illustrating one exemplary embodiment of a mechanical tunneling device 86 that may be used to tunnel between the two buttock incisions 60A and 60B. As will be appreciated by those skilled in the art, tunneling device 86 may be inserted through one of the first or second incisions 60A or 60B such that it is centered beneath the ano-rectum. During insertion, tunneling device 86 is in a narrow configuration with a first spring portion 87A and a second spring portion 87B in a collapsed state. Then, once the tunneling device 86 is centered beneath the ano-rectum, the first and second spring portions 87A and 87B are structured to "spring" open as illustrated by the arrows in FIG. 49 in order to dilate the path between the first and second incisions 60A and 60B.

FIG. 50 is a diagram illustrating the mechanical tunneling device 86 of FIG. 49 in place between the two buttock incisions 60A and 60B. As will be appreciated by those skilled in the art, the mechanical tunneling device 86 may further include "fins" that are structured to gently cut through the subcutaneous tissue to create an open tunnel for the sling.

FIG. 51 illustrates one exemplary alternative embodiment of a mechanical tunneling device 88 that may be used to tunnel between the two buttock incisions 60A and 60B. Particularly, the mechanical tunneling device 88 includes a balloon 89 structured to be inflated in order to dilate the path between the incisions. As will be appreciated by those skilled in the art, and similar to the embodiments of the fluid-filled sacs previously described with reference to FIGS. 24-29, balloon 89 may be filled with any suitable fluid without departing from the intended scope of the present invention. Again, "fluid" should be understood to include gasses, liquids, and semisolid media (such as gels). Additionally, the balloon 89 may have a port operably coupled thereto for adding or removing fluid. The port may be coupled to a tube extending from the balloon 89, which may in turn be disposed within the main body of the mechanical tunneling device 88 so that it is accessible outside of one of the incisions.

Figure 52:
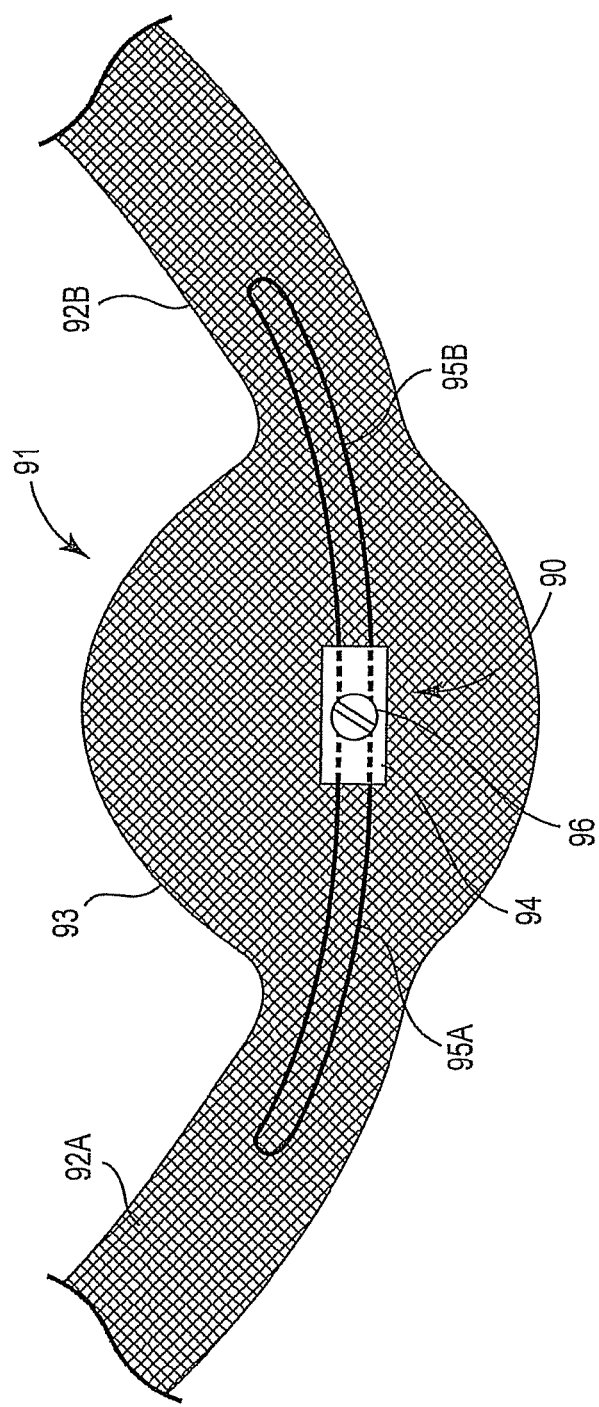
FIG. 52 illustrates one exemplary embodiment of an adjustable device located at the center of a sling that has sutures that are looped through sling arms, wherein the adjustable device is structured for tightening and loosening of the sling.
Figure 53:
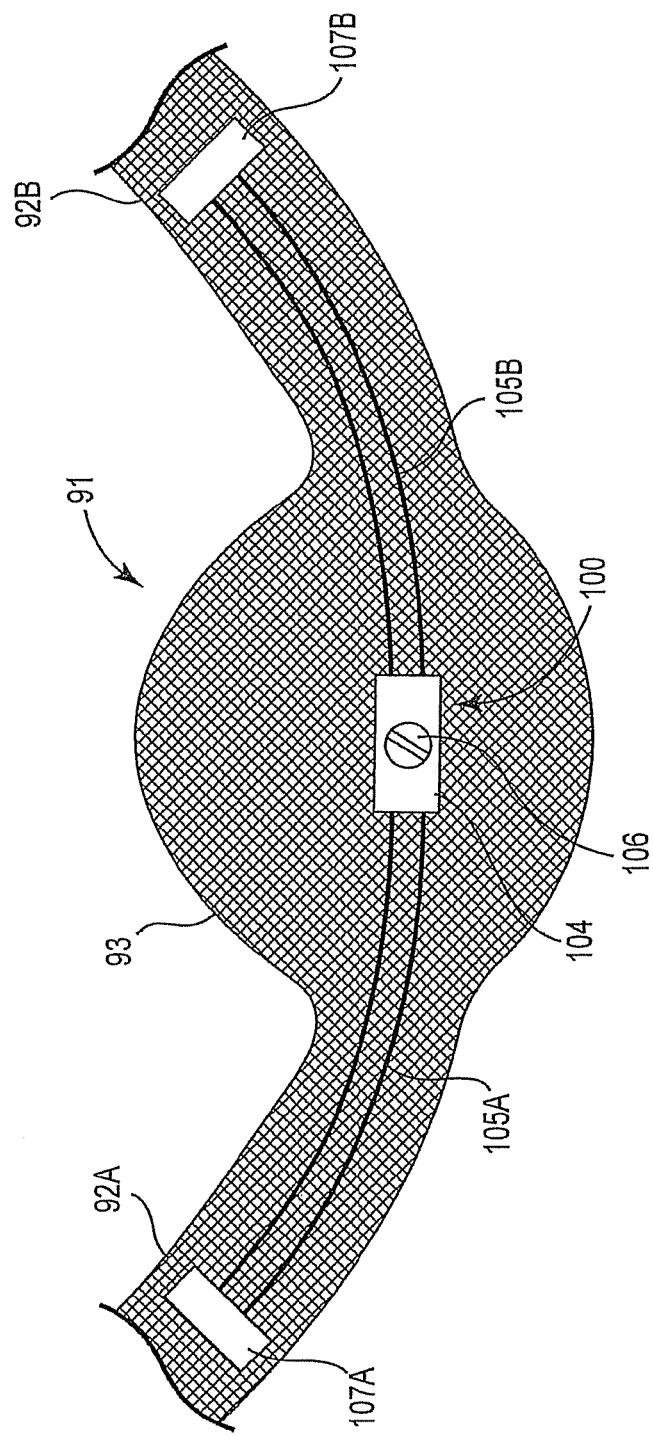
FIG. 53 illustrates another exemplary embodiment of an adjustable device located at the center of the sling that has sutures that extend up to a fixed device located on the sling arms.
Figure 54:
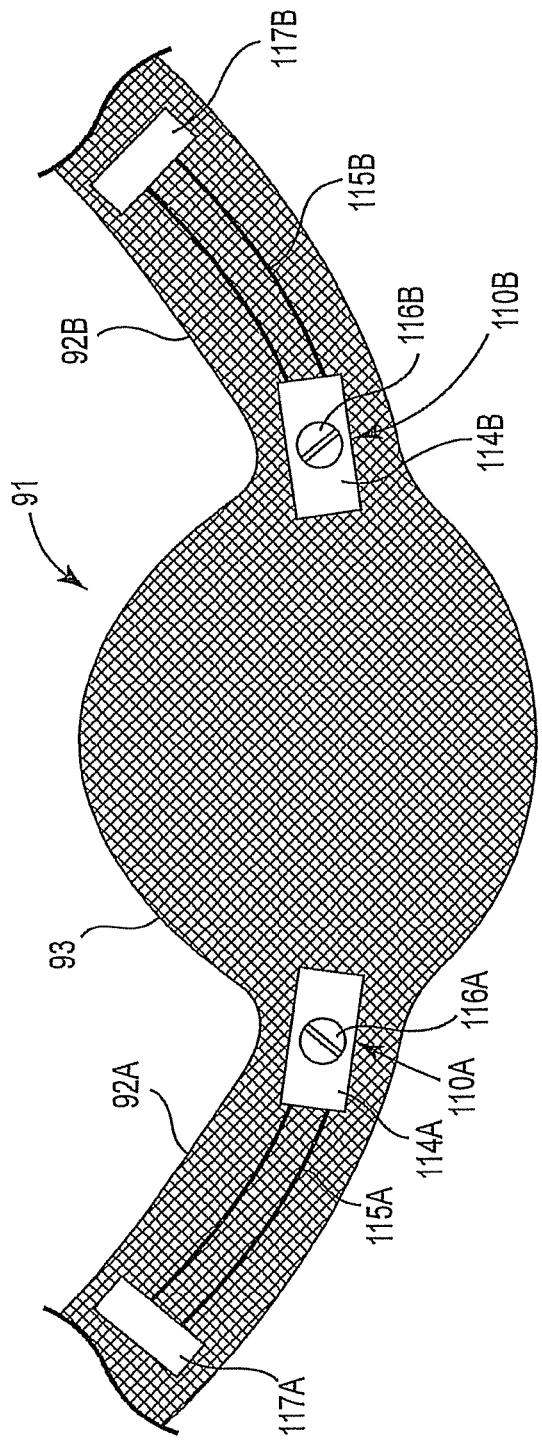
FIG. 54 illustrates yet another exemplary embodiment of an adjustable sling that includes two adjustable devices located on opposing sides of the sling that have sutures that extend up to fixed devices on the sling aims.

In accordance with another aspect of the present invention, there may be a device located on the inferior surface of the belly or central portion of the sling that may be adjusted post-operatively in order to adjust the position of the sling after implantation in the patient. Exemplary devices are illustrated in FIGS. 52-54. Particularly, FIG. 52 a first exemplary embodiment of an adjustable device 90 positioned on a sling 91 having a first aim 92A, a second arm 92B, and a belly or central portion 93 disposed between the first and second arms 92A and 92B. As illustrated in FIG. 52, the adjustable device 90 includes a housing 94, a first suture 95A, and a second suture 95B. The first suture 95A extends out of a first end of the housing 94 and up along the first sling arm 92A where it is looped therethrough to couple the first suture 95A to the first sling arm 92A. Similarly, the second suture 95B extends out of a second end of the housing 94 and up along the second sling arm 92B where it is looped therethrough to couple the second suture 95B to the second sling arm 92B. Rather than being looped through the sling aims, the first and second sutures 95A and 95B may be coupled to the respective sling aims via any suitable connection means, such as by tying the sutures to the sling arms or adhering the sutures to the sling arms with an adhesive.

As further illustrated in FIG. 52, the housing 94 of the adjustable device 90 includes an adjustment means 96 for adjusting the position and length of the sutures 95A and 95B. As will be appreciated by those skilled in the art, making adjustments with adjustment means 96 functions to either draw the first and second sutures 95A and 95B into the housing 94 in order to tighten the sling 91, or to allow the first and second sutures 95A and 95B to be "let out" from the housing 94 in order to loosen the sling 91. For instance, rotating the adjustment means 96 in a first direction may cause a tightening of the sling 91, while rotating the adjustment means 96 in a second, opposite direction may cause a loosening of the sling 91.

As will be appreciated by those skilled in the art, any suitable interface between the first and second sutures 95A and 95B and the adjustment means 96 may be used that allows both tightening and loosening of a sling. In one exemplary embodiment, the first and second sutures 95A and 95B are operably coupled to a spool which is controlled by rotational movement of the adjustment means 96. Furthermore, first and second sutures 95A and 95B may be coupled to the same or different spools. Numerous other embodiments are also contemplated and within the intended scope of the present invention.

FIG. 53 illustrates a second exemplary embodiment of an adjustable device 100 positioned on the sling 91 of FIG. 52. Adjustable device 100 is similar to adjustable device 90 of FIG. 52, and includes a housing 104, a first suture 105A, a second suture 105B, and an adjustment means 106. However, rather than being looped through the first sling arm 92A, the first suture 105A is instead coupled to a first sling arm connecting member 107A that is attached to the first sling arm 92A. Similarly, rather than being looped through the second sling arm 92B, the second suture 105B is instead coupled to a second sling arm connecting member 107B.

The first and second sling arm connecting members 107A and 107B may be attached to their respective sling arms in any suitable manner as will be appreciated by those skilled in the art. Furthermore, the first and second sling aim connecting members 107A and 107B may include a surface upon which their respective sutures may slide as the sling is tightened or loosened. Alternatively, the first and second sling ami connecting members 107A and 107B may include a pulley or the like.

FIG. 54 illustrates a third exemplary embodiment wherein first and second adjustable devices 110A and 110B are positioned on opposite ends of the sling 91. The first adjustable device 110A includes a housing 114A, a first suture 115A, and an adjustment means 116A. The first suture 15A is coupled to a first sling arm connecting member 117A that is attached to the first sling aim 92A. Similarly, the second adjustable device 110B includes a housing 114B, a first suture 115B, and an adjustment means 116B. The second suture 115B is coupled to a second sling arm connecting member 117B that is attached to the second sling aim 92B. As will be appreciated by those skilled in the art, first and second adjustable devices 110A and 110B operate similar to adjustable device 100 previously described. However, having separate adjustable devices associated with each sling ami allows for independent tightening and loosening of the slings arms, which may be desirable under certain circumstances.

Figure 55:
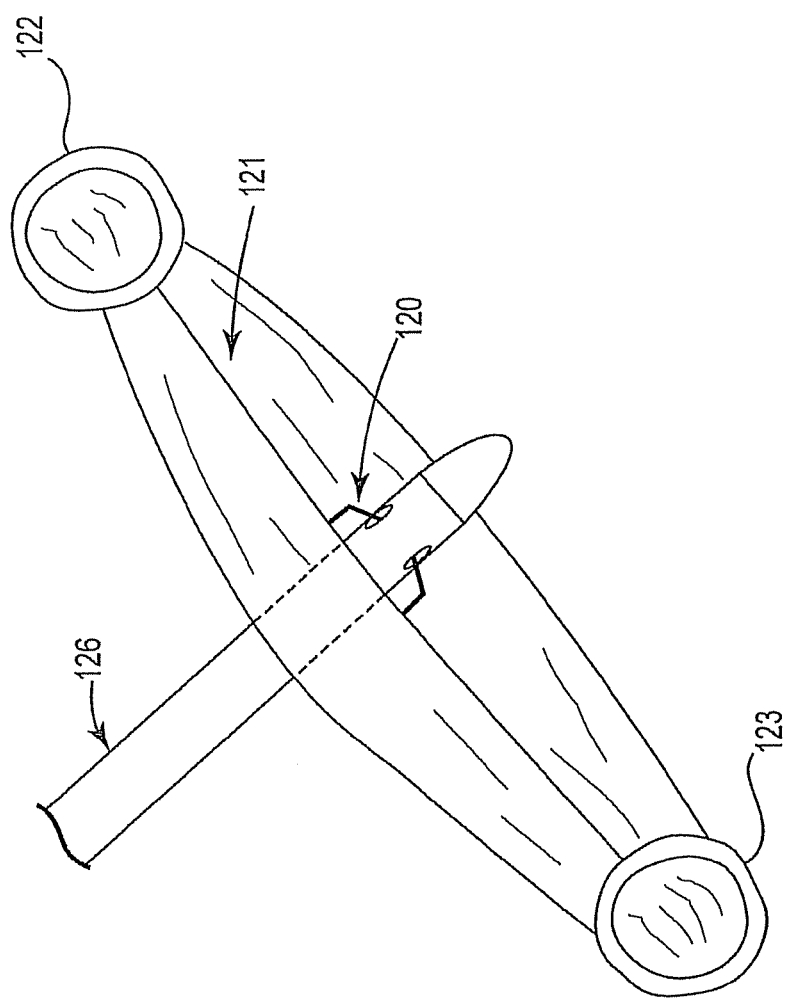
FIG. 55 illustrates one exemplary fascial anchor that is placed on the obturator fascial membrane with the use of an introducer needle.

During surgical placement of a sling, rather than having to pull a sling arm through a thigh incision and cut the sling arm close to the patient's skin such that any excess portion of the sling arm protruding outward from the thigh incision is removed as previously described, an anchoring device may instead be positioned on the obturator membrane that is structured to anchor the sling aim on the obturator membrane. Particularly, FIG. 55 illustrates a fascial anchor 120 that may be placed on the obturator fascial membrane 121 between the pubis 122 and the ischium 123. Although the fascial anchor 120 may be placed on the obturator membrane with any suitable insertion means, one exemplary insertion means may be an introducer needle 126.

Once the fascial anchor 120 has been attached to the obturator membrane 121, a sling arm may be inserted through the anchor 120 in order to secure the sling aim to the anchor. The fascial anchor 120 may be either a unidirectional or a bidirectional device that grips the sling aim, which once again may be fanned from any suitable material including a mesh material, or alternatively solid polypropylene or silicon. The fascial anchor 120 may be placed or deployed during needle placement, such as when the surgeon feels that the obturator membrane has been pierced, or may alternatively be placed after the sling aim has been drawn up through the thigh incision, as it can be threaded onto the sling and seated on or near the obturator membrane.

Figure 56:
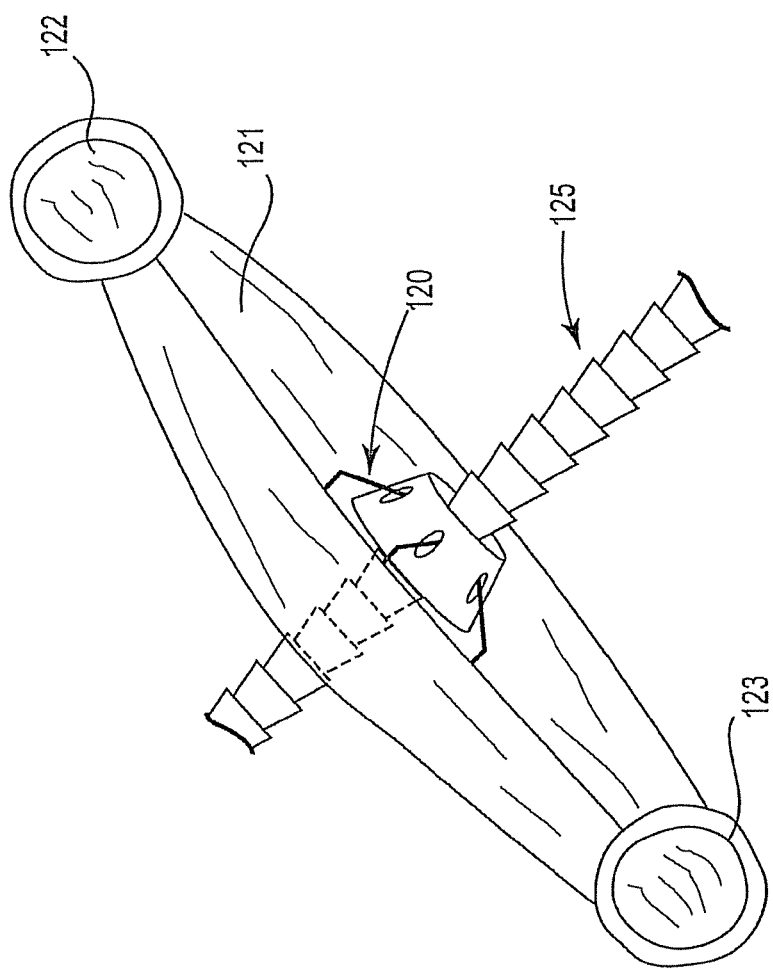
FIG. 56 illustrates the fascial anchor of FIG. 55 with a serrated mesh arm passing through the anchor.

FIG. 56 illustrates the fascial anchor 120 with a serrated mesh arm 125 of a sling device passing through the anchor. As will be appreciated by those skilled in the art, the serrated mesh aim 125 may be operably combined with a unidirectional anchor such that once the mesh aim 125 in inserted though the fascial anchor 120, the sling can only be tightened and not loosened. Stated alternatively, the serrations on the mesh aim 125 may interact with the anchor 120 such that the mesh aim 125 cannot be pulled out in a backward direction once it has been inserted through the fascial anchor 120. This prevents the sling from loosening once it has been positioned within the patient and tightened to the desired "tightness" level. Alternatively, as stated above, a bidirectional anchor may be used that allows the sling to be loosened if it is determined that the sling is too tight.

Figure 57:
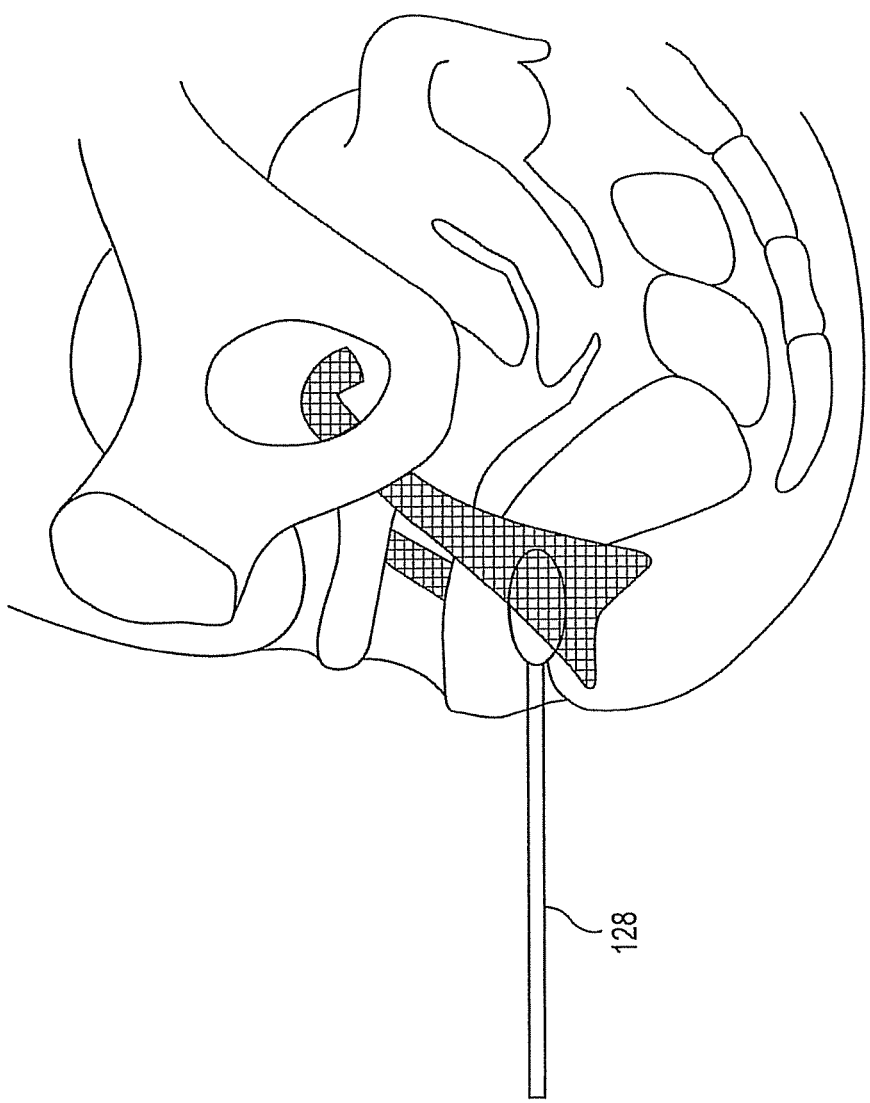
FIG. 57 demonstrates a transrectal manometry device that may be used to determine the tension on a sling.

As will be appreciated by those skilled in the art, when determining the optimal position of a sling within a patient, it may be helpful for the physician to know the amount of tension that should be placed on the ano-rectum. This may be accomplished with a sling tensioning instrument, which is a device that measures pressure or deflection of the rectum in order to determine sling tension. FIG. 57 demonstrates one exemplary embodiment of a transrectal manometry device 128 being used to determine the tension on the sling.

Figure 58:
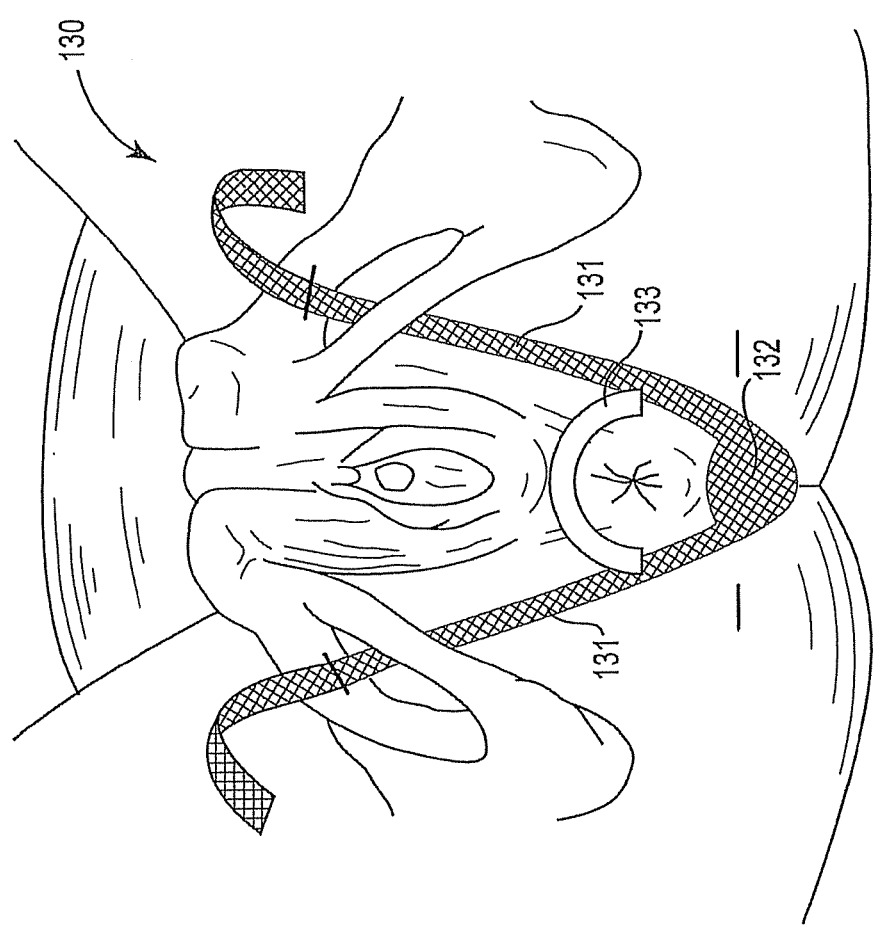
FIG. 58 illustrates an alternative sling embodiment that includes an anterior extension that encircles the anal sphincter in order to provide increased anterior support.

Although numerous slings have been previously illustrated and described, one common element of these slings is that they only include a central portion that is positioned beneath, for example, the ano-rectum. However, as those skilled in the art will appreciate, slings having anterior extension portions are also contemplated. For instance, FIG. 58 illustrates a sling 130 similar to sling 16 previously described with reference to FIG. 3 that includes a pair of arms 131 and a belly or central portion 132 disposed therebetween. However, the sling 130 further includes an anterior extension 133 that is structured to encircle the anal sphincter in order to provide additional anterior support. In the exemplary embodiment shown, the anterior extension 133 may be placed anterior to the anus and attached to the sling aims 131 or lateral portion of the sling central portion 132. This positioning may constrict the anal canal and improve anal continence.

Figure 59:
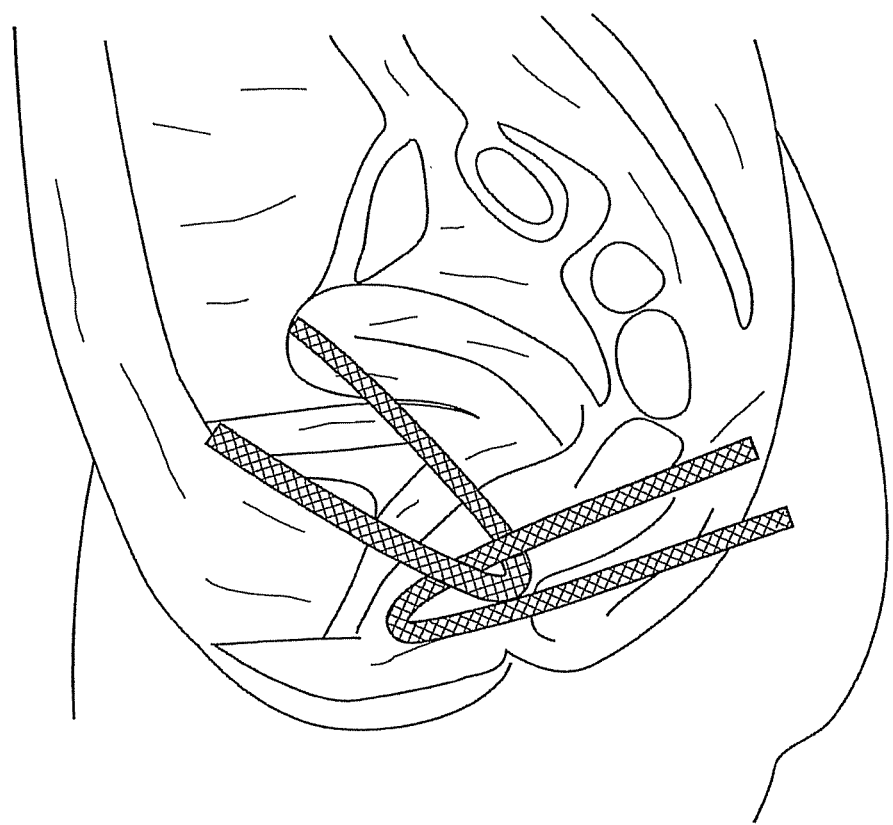
FIG. 59 illustrates two slings placed in a patient, including a transobturator post-anal sling and another sling placed anterior to the anal sphincter in the perineal body, which passes back through the ischiorectal fossa and out the buttocks.

The surgical procedures of the present invention have previously been described herein with reference to a single sling. However, it should be understood that more than one sling may be implanted within a patient without departing from the intended scope of the present invention. For instance, FIG. 59 is a diagram illustrating the placement of two slings within the patient. Particularly, FIG. 59 shows both a transobturator post-anal sling and another sling placed anterior to the anal sphincter in the perineal body, which passes back through the ischiorectal fossa and out the buttocks.

A sling may be performed concomitantly that passes anterior to the anus (in the perineal body), and the aims of the sling may be passed either medial or lateral to the levator ani muscle and may either exit through the buttock skin, possibly passing through the gluteus maximus muscle or may be fixed to the sacrospinous ligament using, for example, plastic anchors.

The various sling embodiments previously described and illustrated have all been relatively narrow in width. However, as those skilled in the art will appreciate, a wider sling could be used with, for example, four or more fixation points: two straps passing in a standard manner through the obturator membrane and two more straps passing posteriorly either through the gluteus maximus muscle and out through the buttocks or fixed to the sacrospinous ligament with tissue anchors or the like.

Figure 60:
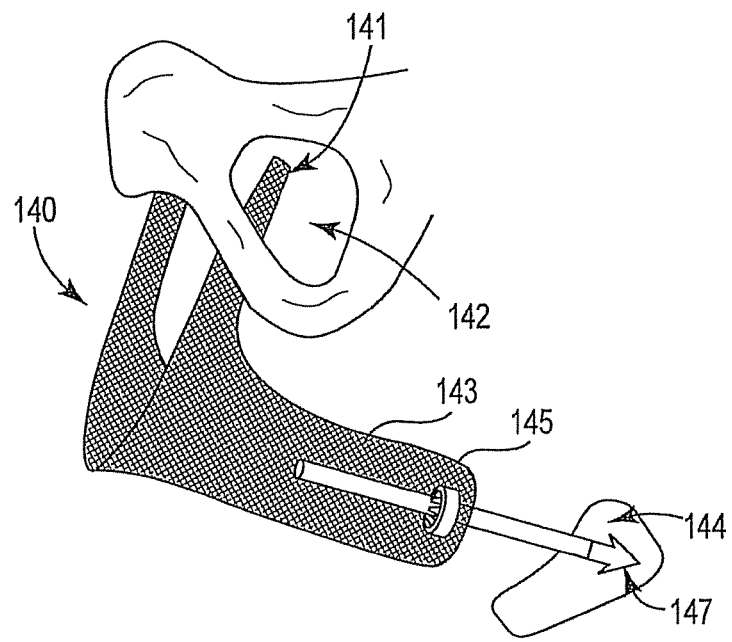
FIG. 60 illustrates one exemplary embodiment of a larger levator sling placed through the ischiorectal fossa that has transobturator mesh straps adjacent the obturator foramen as well as adjustable mesh straps anchored into the sacrospinous ligament.

FIG. 60 illustrates one exemplary embodiment of a larger levator sling 140, placed through the ischiorectal fossa, that has transobturator mesh straps 141 adjacent the obturator foramen 142 and adjustable mesh straps 143 that are anchored into the sacrospinous ligament 144. As further illustrated in FIG. 61, these mesh straps 143 may be passed through rings 145 with tines 146 that extend into the middle of the ring, which are located on the proximal lateral portions of the mesh straps 143.

Figure 61:
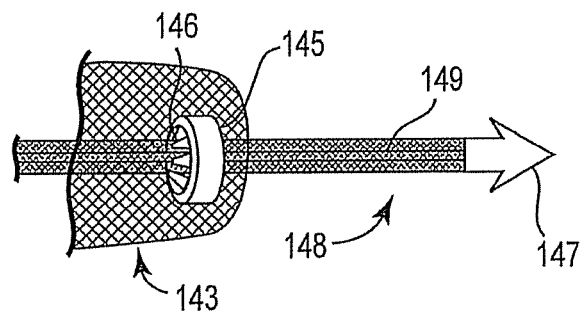
FIG. 61 is an enlarged view of an adjustable mesh strap of FIG. 60.

If anchors 147 are used in the sacrospinous ligament as illustrated in FIGS. 60-61, the anchors 147 could be attached to a strap of mesh 148 which may include a stiff polypropylene rod 149 on the end. These rods 149 may be placed through the rings 145 attached to the corners of the proximal mesh. As stated above, the rings 145 may have tines 146 or other devices that extend into the center of the ring and grasp the mesh, so that the mesh can be tightened by pulling it through the rings until the proper tension is attained.

Figure 62:
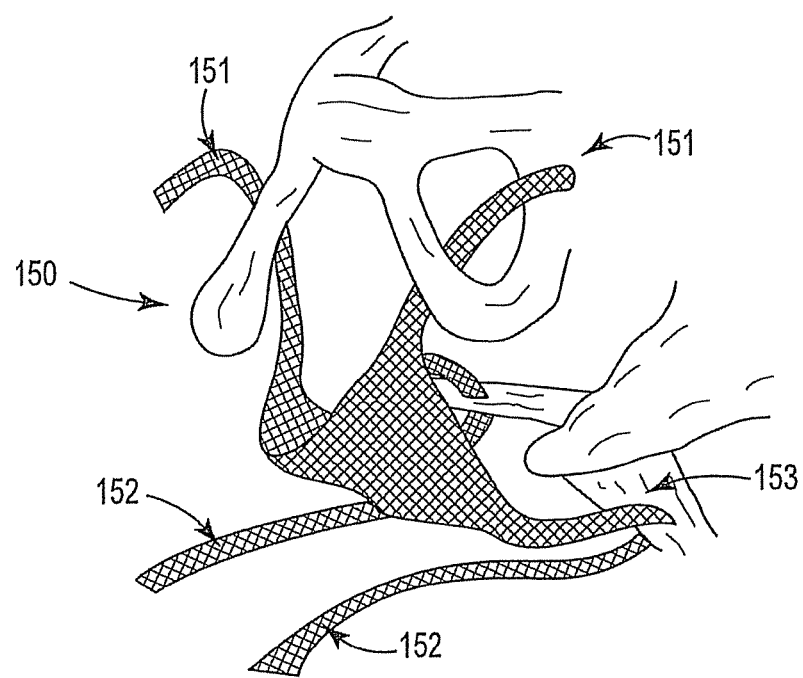
FIG. 62 illustrates another exemplary embodiment of a larger levator sling passed through the ischiorectal fossa that has transobturator mesh straps as well as proximal lateral mesh straps that are passed through the sacrospinous ligament.

FIG. 62 illustrates another exemplary embodiment of a larger levator sling 150, passed through the ischiorectal fossa, that has transobturator mesh straps 151 and proximal lateral mesh straps 152 that are passed through the sacrospinous ligament 153 and can be adjusted before final closure of the skin incisions. Alternatively, the proximal mesh straps 152 could be placed through the sacrospinous ligament 153 and the straps could then come out through a posterior buttock incision and be used to adjust the tension of the sling. In this embodiment, all four mesh straps could be used to adjust the tension on the levator support.

FIGS. 63-64 illustrate an alternative embodiment of a sling in accordance with another aspect of the present invention. Particularly, FIGS. 63-64 illustrate an exemplary sling 160 having a belly or central portion 161 that includes a first ring 162A adjacent to a first end of the central portion 161 and a second ring 162B adjacent to a second end of the central portion 161. The first and second rings 162A and 162B may be formed from any suitable material, such as a plastic.

As illustrated in FIGS. 63-64, mesh straps or arms 164 placed through the obturator membrane, into the ischiorectal fossa, and out through the lateral buttock incisions, may be loaded onto the rings 162A and 162B on the lateral edges of the mesh central portion 161, and may then be pushed up to tighten the sling such that the central portion 161 is disposed beneath the rectum 166. As illustrated in FIG. 65, which is an enlarged view of one end of the central portion 161 of the sling 160 showing the second ring 162B, the rings may have a plurality of tines 167 or similar devices extending into an open center thereof. As will be appreciated by those skilled in the art, when a sling aim is passed through the open center portion of the ring, the sling aim may engage the tines 167.

Once the sling 160 is positioned within the patient, the belly or central portion 161 is advanced in an upward direction toward the rectum 166 with tension placed on either sling arm 164. The first and second rings 162A and 162B may be unidirectional devices, only permitting tightening and not loosening However, bidirectional devices are also contemplated. Once the sling 160 is determined to be in its final position, the arms 164 may be cut below the level of the rings 162A and 162B (and sling central portion 161), possibly with a device that is threaded over the sling arm and that can be advanced up into the ischiorectal fossa in order to cut the arm.

Optionally, as illustrated in FIG. 64, a pair of donut-like fastener members 168 may be positioned adjacent the obturator membrane 169 in order to anchor the end of the sling arms 164 that is opposite the central portion 161 of the sling 160.

Figure 66:
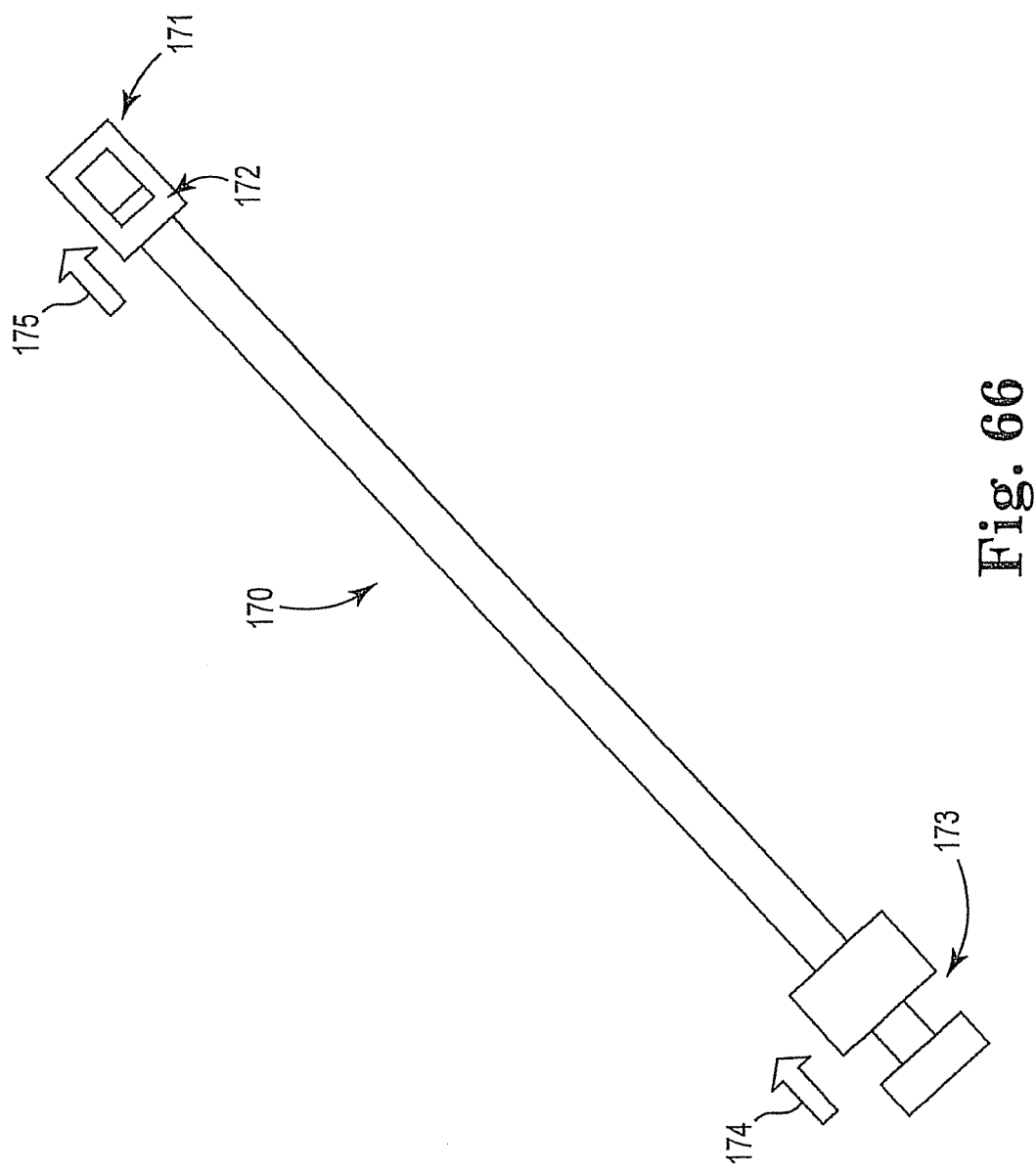
FIG. 66 is a diagram illustrating one exemplary instrument that can be used to push the central portion of the sling of FIGS. 63-64 up on the sling arms in order to tighten the sling.

FIG. 66 is a diagram illustrating one exemplary instrument 170 that can be used to push the central portion 161 of the sling 160 with the first and second lateral rings 162A and 162B up onto the sling aims 164 in order to tighten the sling. As will be appreciated by those skilled in the art, an end of a sling arm may be positioned through a closed loop 171 in a distal end of the instrument 170. The instrument may also have a retractable blade 172 that may be operated with a blade activation button 173 located at a proximal end of the instrument 170. Upon pushing the activation button 173 in the direction indicated by arrow 174, the retractable blade 172 is structured to move in the corresponding direction indicated by arrow 175 in order to cut the sling aim after the sling has been adjusted to the desired position.

Although the present invention has been described with reference to preferred embodiments, workers skilled in the art will recognize that changes may be made in faun and detail without departing from the spirit and scope of the invention.

What is claimed:

1. A system for reducing anal incontinence comprising: a sling structured to be implanted in a patient, the sling including a central portion; at least two arms coupled to said central portion and extending laterally therefrom; and one or more sub-rectal extension elements structured for attachment to a coccyx of the patient and coupled to said central portion, wherein the central portion has a shape that is wider than said at least two arms and which, after implantation, is structured to conform to the external contour of the anus, rectum, ano-rectal angle and/or levator ani muscles in said patient.

2. The system of claim 1 further including an introducer needle having a needle tip and a needle shaft, said introducer needle attachable to said arms for positioning said arms through an obturator formen.

3. The system of claim 2 wherein said introducer needle further comprises a hollow sheath covering said introducer needle.

4. The system of claim 2 wherein said needle tip is threadably removable from said needle shaft.

5. The system of claim 4 further including a male-connector screw having a threaded end and a non-threaded end, said non-threaded end coupled to said arms.

6. The system of claim 5 wherein said male-connector screw is structured to threadably couple to said needle shaft upon removal of said needle tip.

7. The system of claim 2 wherein said needle tip comprises a jaw for grasping said arms.

8. The system of claim 3 wherein said arms further include a suture coupled thereto.

9. The system of claim 8 wherein said sheath includes a spring-mechanism for deploying the needle tip.

10. The system of claim 8 or 9 wherein said needle tip includes a notch for operably coupling to said suture.

11. The system of claim 1 wherein the central portion includes an adjustably inflatable sac.

12. The system of claim 11 wherein said adjustably inflatable sac further includes a subcutaneously accessible port positioned at a bottom of the central portion for the introduction and removal of fluid.

13. The system of claim 11 wherein said adjustably inflatable sac further includes connector tubing having first and second ends, said connector tubing coupled to said sac at said first end and having a port coupled thereto at said second end for introducing fluid into and removing fluid from said sac.

14. The system of claim 1 wherein said arms include serrations thereon for maintaining said sling in position after implantation.

15. The system of claim 1 further comprising fixation devices for attaching said arms to pelvic bone, said fixation devices selected from the group consisting of bone anchors, suture material and combinations thereof.

16. The system of claim 1 wherein said one or more sub-rectal extension elements comprise rigid, semi-rigid or flexible elements coupled to said central portion in a direction transverse to the length of the sling.

17. The system of claim 1 further comprising a measuring device for measuring the angle made between the anus and rectum, said measuring device having a proximal ring and a distal ring operably connected by joint wherein said angle is displayed on a visual scale coupled to said proximal ring.

18. The system of claim 17 wherein said measuring device is structured to fit over a finger.

19. The system of claim 1 wherein each arm includes a removable sheath for facilitating passage through an obturator foramen.

20. The system of claim 1 wherein the sling comprises a material selected from the group consisting of a synthetic material, a natural xenograft material, an allograft material and combinations thereof.

21. The system of claim 19 wherein each arm of the sling is made from elastic material.

22. The system of claim 1 further comprising a first connector coupled to an end of a first one of said at least two arms, said first connector comprising a first ring-shaped member; and a second connector coupled to an end of a second one of said at least two arms, said second connector comprising a second ring-shaped member.

23. The system of claim 1 further comprising an adjustable device coupled to the inferior surface of the central portion, the adjustable device including a housing and adjustment means for adjusting a tension of the first and second sling arms; said adjustment means coupled to said housing, wherein rotating the adjustment means in a first direction increases the tension of the first and second sling arms, and wherein rotating the adjustment means in a second, opposite direction decreases the tension of the first and second sling arms.

24. The system of claim 22, wherein the first sling arm is insertable though an open center of the first ring-shaped member, and wherein the second sling arm is insertable though an open center of the second ring-shaped member.

25. The system of claim 24, wherein the first and second ring-shaped members each include a plurality of tines extending toward the open center of the ring-shaped members.

26. The system of claim 1, wherein said at least two anus are formed from a mesh material.

27. The system of claim 1, wherein the first and second sling anus each include a serrated portion.

28. The system of claim 22, wherein the first and second connectors are unidirectional devices that allow tightening of the first and second sling arms.

29. The sling of claim 22, wherein the first and second connectors are bidirectional devices that allow both tightening and loosening of the first and second sling arms.

30. The system of claim 1 wherein said central portion comprises a preformed curved shape.

31. The system of claim 1 wherein said sub-rectal portion includes an extension coupled to an inferior portion thereof, said extension structured to be fixed to the coccyx.

32. The system of claim 1 wherein said sub-rectal portion includes a posterior aspect that is structured to be coupled to the coccyx.

* * * * *

UNITED STATES PATENT AND TRADEMARK OFFICE
CERTIFICATE OF CORRECTION

PATENT NO. : 8,678,991 B2  
APPLICATION NO. : 13/438556  
DATED : March 25, 2014  
INVENTOR(S) : Rosenblatt Page 1 of 1

It is certified that error appears in the above-identified patent and that said Letters Patent is hereby corrected as shown below:

On the Title Page, in Item (57), under "ABSTRACT", in Column 2, Line 16, delete "sling aim" and insert -- sling arm --, therefor.

In the Specification;  
    Column 2, Line 51, delete "natural" and insert -- normal --, therefor.  
    Column 4, Line 20, delete "aim" and insert -- arm --, therefor at each occurrence throughout the Specification; Column 4, Line 52, delete "alms." and insert -- arms --, therefor.  
    Column 5, Line 2, delete "aims" and insert -- arms --, therefor at each occurrence throughout the Specification.  
    Column 8, Line 6, delete "The of" and insert -- The arms of --, therefor; Column 8, Line 48, delete "amts." and insert -- arms. --, therefor.  
    Column 9, Line 18, delete "anus" and insert -- arms --, therefor.  
    Column 10, Line 31, delete "ami" and insert -- arm --, therefor at each occurrence throughout the Specification.  
    Column 12, Line 51, delete "pair of anus" and insert -- pair of arms --, therefor.  
    Column 14, Line 51, delete "161" and insert -- 16I --, therefor; Column 14, Line 52, delete "171." and insert -- 17I. --, therefor.  
    Column 15, Line 9, delete "fixated" and insert -- formed --, therefor.  
    Column 18, Line 32, delete "sling" and insert -- sling arm --, therefor.  
    Column 20, Line 63, delete "fanned" and insert -- formed --, therefor.  
    Column 22, Line 60, delete "loosening However," and insert -- loosening. However, --, therefor.  
    Column 23, Line 20, delete "faun" and insert -- form --, therefor.

Signed and Sealed this  
Tenth Day of February, 2015

Michelle K. Lee  
*Deputy Director of the United States Patent and Trademark Office*